(12) United States Patent
Kim et al.

(10) Patent No.: US 12,045,424 B2
(45) Date of Patent: Jul. 23, 2024

(54) DISPLAY DEVICE, SENSING UNIT, AND SENSING METHOD

(71) Applicants: Samsung Display Co., Ltd., Yongin-Si (KR); UNIST (ULSAN NATIONAL INSTITUTE OF SCIENCE AND TECHNOLOGY), Ulsan (KR)

(72) Inventors: Yu Na Kim, Seoul (KR); Ki Bog Park, Ulsan (KR); Sung Chul Jung, Icheon-si (KR); Jun Hyung Kim, Ulsan (KR)

(73) Assignees: Samsung Display Co., Ltd., Yongin-si (KR); UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 65 days.

(21) Appl. No.: 16/986,267

(22) Filed: Aug. 6, 2020

(65) Prior Publication Data

US 2021/0041987 A1  Feb. 11, 2021

(30) Foreign Application Priority Data

Aug. 6, 2019 (KR) .................. 10-2019-0095417

(51) Int. Cl.
*G06F 3/041* (2006.01)
*G06F 3/044* (2006.01)
(Continued)

(52) U.S. Cl.
CPC .......... *G06F 3/0445* (2019.05); *G06F 3/0412* (2013.01); *H10K 50/84* (2023.02); *H10K 59/40* (2023.02); *G06F 2203/04105* (2013.01)

(58) Field of Classification Search
None
See application file for complete search history.

(56) References Cited

U.S. PATENT DOCUMENTS

2017/0112445 A1*  4/2017  Wang ................. A61B 5/486
2019/0012016 A1*  1/2019  Kurasawa ........... G06F 3/04164
(Continued)

FOREIGN PATENT DOCUMENTS

JP  2003-156464 A  5/2003
JP  2016-161486 A  9/2016
(Continued)

OTHER PUBLICATIONS

Hanbyul Jin et al., "Stretchable Dual-Capacitor Multi-Sensor for Touch-Curvature-Pressure-Strain Sensing", Scientific Reports, Sep. 7, 2017, pp. 1-8.

(Continued)

*Primary Examiner* — Brian M Butcher
(74) *Attorney, Agent, or Firm* — Innovation Counsel LLP

(57) ABSTRACT

A sensing unit includes a base, first electrodes, an insulating layer, second electrodes, and third electrodes. The first electrodes are arranged on the base, extend in a first direction, and are spaced apart from each other in a second direction different from the first direction. The first insulating layer is disposed on the first electrodes. The second electrodes are electrically insulated from the first electrodes by the insulating layer, extend in the second direction, and are spaced apart from each other in the first direction. The third electrodes are electrically insulated from the first electrodes by the insulating layer, extend in the second direction, and are electrically insulated from the second electrodes. The second electrodes and the third electrodes are alternately arranged in the first direction. The third electrodes may receive a driving signal or a sensing signal according to a sensing mode.

19 Claims, 23 Drawing Sheets

(51) Int. Cl.
*H10K 50/84* (2023.01)
*H10K 59/40* (2023.01)

(56) References Cited

U.S. PATENT DOCUMENTS

2019/0369799 A1* 12/2019 Jeon ...................... G06F 3/0448
2020/0305740 A1* 10/2020 Quan ................. A61B 5/02108

FOREIGN PATENT DOCUMENTS

| KR | 10-0634544 B1 | 10/2006 |
| KR | 10-0938403 B1 | 1/2010 |
| KR | 10-1022904 B1 | 3/2011 |
| KR | 10-1462283 B1 | 11/2014 |
| KR | 2017-0125933 A | 11/2017 |
| KR | 2018-0048179 A | 5/2018 |

OTHER PUBLICATIONS

Hayato Fukushima et al. "Estimating heart rate using wrist-type photoplethysmography and acceleration sensor while running", IEEE, Aug. 28, 2012, pp. 2901-2904.

* cited by examiner

AE : AE1, AE2
E2_1 : E2a, E2b
E3_1 : E3a, E3b

EMA : EMA_R, EMA_B, EMA_G
E : E1, E2, E3

DISPLAY DEVICE, SENSING UNIT, AND SENSING METHOD

This application claims priority to Korean Patent Application No. 10-2019-0095417, filed on Aug. 6, 2019 in the Korean Intellectual Property Office; the disclosure of the Korean Patent Application is incorporated herein by reference in its entirety.

BACKGROUND

1. Field

The technical field relates to a display device including a sensing unit and a sensing method.

2. Description of the Related Art

Display devices may be included in various electronic devices for displaying images to users. The electronic devices may include, for example, smartphones, tablet computers, digital cameras, notebook computers, navigators, and televisions.

A display device may include a display panel for transmitting and/or emitting light to display images. The display device may further include a sensor, such as an optical sensor, for performing one or more sensing functions. An optical sensor may require a light source and may therefore undesirably increase power consumption and/or manufacturing cost of the display device.

SUMMARY

Embodiments may be related to a sensing unit capable of sensing a heart rate without a light source. Embodiments may be related to a display device including the sensing unit.

Embodiments may be related to a sensing method of sensing a heart rate without a light source.

According to an embodiment, a sensing unit includes a base, first electrodes arranged on the base, extending in a first direction, and spaced apart from each other in a second direction intersecting the first direction, a first insulating layer disposed on the first electrodes, second electrodes arranged on the first insulating layer, extending in the second direction, and spaced apart from each other in the first direction, and third electrodes arranged on the first insulating layer, extending in the second direction, and alternately arranged with the second electrodes in the first direction, wherein the third electrodes are configured to receive a driving signal or receive a sensing signal according to a sensing mode.

In an embodiment, the sensing unit further includes a sensing driving circuit applying a signal to the first electrodes, the second electrodes, and the third electrodes, first lines connecting the first electrodes and the sensing driving circuit, second lines connecting the second electrodes and the sensing driving circuit, and third lines connecting the third electrodes and the sensing driving circuit, wherein each of the third lines is connected to the sensing driving circuit through a first switch and a second switch connected in parallel with each other.

In an embodiment, the sensing unit further includes a controller supplying a control signal to the first switch and the second switch.

In an embodiment, the controller supplies the control signal to the first switch to turn on the first switch in a touch input and pressure sensing mode, wherein the controller supplies the control signal to the second switch to turn on the second switch in a heart rate sensing mode, and wherein the sensing driving circuit applies the driving signal to the third lines when the first switch is turned on and receives the sensing signal from the third lines when the second switch is turned on.

In an embodiment, wherein the sensing driving circuit receives the sensing signal from the first lines and applies the driving signal to the second lines in the touch input and pressure sensing mode, and wherein the sensing driving circuit applies a ground voltage to the first lines and applies the driving signal to the second lines in the heart rate sensing mode.

In an embodiment, the first electrodes and the second electrodes are spaced apart from each other in the first direction, and a distance between the first electrode and the second electrode is about 2 mm to about 4 mm.

In an embodiment, the sensing unit further includes a second insulating layer disposed on the second electrodes and the third electrodes, wherein each of the first insulating layer and the second insulating layer includes polydimethylsiloxane (PDMS).

In an embodiment, the first electrodes, the second electrodes, and the third electrodes include at least one of Ag nanowire, metal mesh, and carbon nanotube (CNT).

In an embodiment, the sensing unit further includes first auxiliary electrodes arranged on one side of the second electrodes; and second auxiliary electrodes arranged on one side of the third electrodes, wherein the first auxiliary electrodes and the second auxiliary electrodes are alternately arranged, are spaced apart from each other, and a distance between the first auxiliary electrode and the second auxiliary electrode is about 10 um to about 500 um.

According to another embodiment of the disclosure, a display device, includes a display unit, a sensing unit disposed on the display unit, and a window member disposed on the sensing unit, wherein the sensing unit includes a base, first electrodes arranged on the base, extending in a first direction, and spaced apart from each other in a second direction intersecting the first direction, a first insulating layer disposed on the first electrodes, second electrodes arranged on the first insulating layer, extending in the second direction, and spaced apart from each other in the first direction, and third electrodes arranged on the first insulating layer, extending in the second direction, and alternately arranged with the second electrodes in the first direction, wherein the third electrodes are configured to receive a driving signal or receive a sensing signal according to a sensing mode.

In an embodiment, the display device further includes a sensing driving circuit applying a signal to the first electrodes, the second electrodes, and the third electrodes, first lines connecting the first electrodes and the sensing driving circuit, second lines connecting the second electrodes and the sensing driving circuit, and third lines connecting the third electrodes and the sensing driving circuit, wherein each of the third lines is connected to the sensing driving circuit through a first switch and a second switch connected in parallel with each other.

In an embodiment, the display device further includes a controller supplying a control signal to the first switch and the second switch.

In an embodiment, the controller supplies the control signal to the first switch to turn on the first switch in a touch input and pressure sensing mode, the controller supplies the control signal to the second switch to turn on the second switch in a heart rate sensing mode, and the sensing driving circuit applies the driving signal to the third lines when the first switch is turned on and receives the sensing signal from the third lines when the second switch is turned on.

In an embodiment, the sensing driving circuit receives the sensing signal from the first lines and applies the driving signal to the second lines in the touch input and pressure mode, and the sensing driving circuit applies a ground voltage to the first lines and applies the driving signal to the second lines in the heart rate sensing mode.

In an embodiment, the first electrodes and the second electrodes are spaced apart from each other in the first direction, and a distance between the first electrode and the second electrode is about 2 mm to about 4 mm.

In an embodiment, the display unit includes a substrate, a thin film transistor layer disposed on the substrate, a light emitting element layer disposed on the thin film transistor layer; and a thin film encapsulation layer disposed on the light emitting element layer, wherein the base of the sensing unit is disposed on an upper surface of the thin film encapsulation layer.

According to another embodiment of the disclosure, a method of sensing a display device includes sensing a change of a first capacitance in a vertical direction to sense a touch pressure and a touch pressure; and sensing a change of a second capacitance, which is a fringe capacitance, to sense a heart rate.

In an embodiment, first electrodes arranged on the base, extending in a first direction, and spaced apart from each other in a second direction intersecting the first direction; a first insulating layer disposed on the first electrodes; second electrodes arranged on the first insulating layer, extending in the second direction, and spaced apart from each other in the first direction; and third electrodes arranged on the first insulating layer, extending in the second direction, and alternately arranged with the second electrodes in the first direction are provided, and the sensing of the touch pressure and the touch pressure further includes receiving the sensing signal from the first electrodes; and applying a driving signal to the second electrodes and the third electrodes.

In an embodiment, the sensing of the heart rate further includes applying the driving signal to the second electrodes and receiving the sensing signal from the third electrodes In an embodiment, the sensing of the heart rate further includes applying a ground voltage to the first electrodes.

An embodiment may be related to a sensing unit. The sensing unit may include a base, first electrodes, a first insulating layer, second electrodes, and third electrodes. The first electrodes may be arranged on the base, may extend lengthwise individually in a first direction, and may be spaced apart from each other in a second direction different from the first direction. The first insulating layer may be disposed on the first electrodes. The second electrodes may be electrically insulated from the first electrodes by the first insulating layer, may extend lengthwise individually in the second direction, and may be spaced apart from each other in the first direction. The third electrodes may be electrically insulated from the first electrodes by the first insulating layer, may extend lengthwise individually in the second direction, and may be electrically insulated from the second electrodes. The second electrodes and the third electrodes may be alternately arranged in the first direction. The third electrodes may receive a driving signal or a sensing signal according to a sensing mode.

The sensing unit may include the following elements: a sensing driving circuit providing signals to the first electrodes, the second electrodes, and the third electrodes; first lines electrically connecting the first electrodes and the sensing driving circuit; second lines electrically connecting the second electrodes and the sensing driving circuit; and third lines electrically connecting the third electrodes and the sensing driving circuit. The third lines may be connected to the sensing driving circuit through first switches and second switches. Each of the third lines may be connected to the sensing driving circuit through a first switch and a second switch that may be electrically connected in parallel.

The sensing unit may include a controller supplying control signals to the first switches and the second switches.

The controller may supply a first control signal to the first switches to turn on the first switches in a touch input sensing mode. The controller may supply a second control signal to the second switches to turn on the second switches in a heart rate sensing mode. The sensing driving circuit may provide the driving signal to the third lines when the first switches may be turned on and may receive the sensing signal from the third lines when the second switches may be turned on.

The sensing driving circuit may receive the sensing signal from the first lines and may provide the driving signal to the second lines in the touch input sensing mode. The sensing driving circuit may provide a ground voltage to the first lines and may provide the driving signal to the second lines in the heart rate sensing mode.

The second electrodes and the third electrodes may be spaced apart from each other in the first direction. A distance between a second electrode and an immediately neighboring third electrode may be in a range of about 2 mm to about 4 mm.

The sensing unit may include a second insulating layer disposed on the second electrodes and the third electrodes. Each of the first insulating layer and the second insulating layer may include polydimethylsiloxane (PDMS).

The first electrodes, the second electrodes, and the third electrodes include at least one of a silver nanowire, a metal mesh, and a carbon nanotube (CNT).

The sensing unit may include first auxiliary electrodes protruding from one of the second electrodes and may include second auxiliary electrodes protruding from one of the third electrodes. The first auxiliary electrodes and the second auxiliary electrodes may be alternately arranged and may be spaced apart from each other. A distance between a first auxiliary electrode and an immediately neighboring second auxiliary electrode may be in a range of about 10 um to about 500 um.

An embodiment may be related to a display device. The display device may include the following elements: a display unit; a sensing unit disposed on the display unit; and a window member disposed on the sensing unit. The sensing unit may include the following elements: a base; first electrodes arranged on the base, extending lengthwise individually in a first direction, and spaced apart from each other in a second direction different from the first direction; a first insulating layer disposed on the first electrodes; second electrodes electrically insulated from the first electrodes by the first insulating layer, extending lengthwise individually in the second direction, and spaced apart from each other in the first direction; and third electrodes electrically insulated from the first electrodes by the first insulating layer, extending lengthwise individually in the second direction, and electrically insulated from the second electrodes. The second electrodes and the third electrodes may be alternately arranged in the first direction. The third electrodes may receive a driving signal or a sensing signal according to a sensing mode.

The display device may include the following elements: a sensing driving circuit providing signals to the first electrodes, the second electrodes, and the third electrodes; first lines electrically connecting the first electrodes and the sensing driving circuit; second lines electrically connecting the second electrodes and the sensing driving circuit; and third lines electrically connecting the third electrodes and the sensing driving circuit. The third lines may be connected to the sensing driving circuit through first switches and second switches, and wherein each of the third lines may be connected to the sensing driving circuit through a first switch and a second switch that may be electrically connected in parallel.

The display device may include a controller supplying control signals to the first switches and the second switches.

The controller may supply a first control signal to the first switches to turn on the first switches in a touch input sensing mode. The controller may supply a second control signals to the second switches to turn on the second switches in a heart rate sensing mode. The sensing driving circuit may provide the driving signal to the third lines when the first switches may be turned on and may receive the sensing signal from the third lines when the second switches may be turned on.

The sensing driving circuit may receive the sensing signal from the first lines and may provide the driving signal to the second lines in the touch input mode. The sensing driving circuit may provide a ground voltage to the first lines and may provide the driving signal to the second lines in the heart rate sensing mode.

The second electrodes and the third electrodes may be spaced apart from each other in the first direction. A distance between a second electrode and an immediately neighboring third electrode may be in a range of about 2 mm to about 4 mm.

The display unit may include the following elements: a substrate; a thin film transistor layer disposed on the substrate; a light emitting element layer disposed on the thin film transistor layer; and a thin film encapsulation layer disposed between the light emitting element layer and the base of the sensing unit.

An embodiment may be related to a method of sensing performed by a display device. The method may include the following steps: sensing a change of a first capacitance in a vertical direction perpendicular to a face of the display device for sensing of a touch on the display device; and sensing a change of a second capacitance, which may be a fringe capacitance, for sensing of a heart rate.

The display device may include the following elements: a base; first electrodes arranged on the base, extending lengthwise individually in a first direction different from the vertical direction, and spaced apart from each other in a second direction different from the first direction and the vertical direction; a first insulating layer disposed on the first electrodes; second electrodes electrically insulated from the first electrodes by the first insulating layer, extending lengthwise individually in the second direction, and spaced apart from each other in the first direction; and third electrodes electrically insulated from the first electrodes by the first insulating layer, extending lengthwise individually in the second direction, and electrically insulated from the second electrodes. The second electrodes and the third electrodes may be alternately arranged in the first direction may be provided. The third electrodes may receive a driving signal or a sensing signal according to a sensing mode. The sensing of the touch may include the following steps: receiving the sensing signal from the first electrodes; and providing a driving signal to the second electrodes and the third electrodes.

The sensing of the heart rate may include the following steps: providing the driving signal to the second electrodes; and receiving the sensing signal from the third electrodes.

The sensing of the heart rate may include providing a ground voltage to the first electrodes.

DETAILED DESCRIPTION OF EMBODIMENTS

Example embodiments are described with reference to the accompanying drawings. This invention may be embodied in different forms and should not be construed as limited to the described embodiments.

Although the terms "first," "second," etc. may be used to describe various elements, these elements should not be limited by these terms. These terms are used to distinguish one element from another element. For instance, a first element may be termed a second element without departing from the teachings of one or more embodiments. The description of an element as a "first" element may not require or imply the presence of a second element or other elements. The terms "first," "second," etc. may be used to differentiate different categories or sets of elements. For conciseness, the terms "first," "second," etc. may represent "first-type (or first-set)," "second-type (or second-set)," etc., respectively.

When a first element is referred to as being "on" a second element, the first element can be directly on the second element, or one or more intervening elements may be present between the first element and the second element. When a first element is referred to as being "directly on" a second element, there are no intervening elements (except for environmental elements such as air) present between the first element and the second element.

The term "connect" may mean "electrically connect." The term "insulate" may mean "electrically insulate" or "electrically isolate." The term "contact" may mean "directly contact" or "direct contact." The expression that an element extends in a specified direction may mean that the lengthwise direction of the element is the specified direction.

Figure 1:
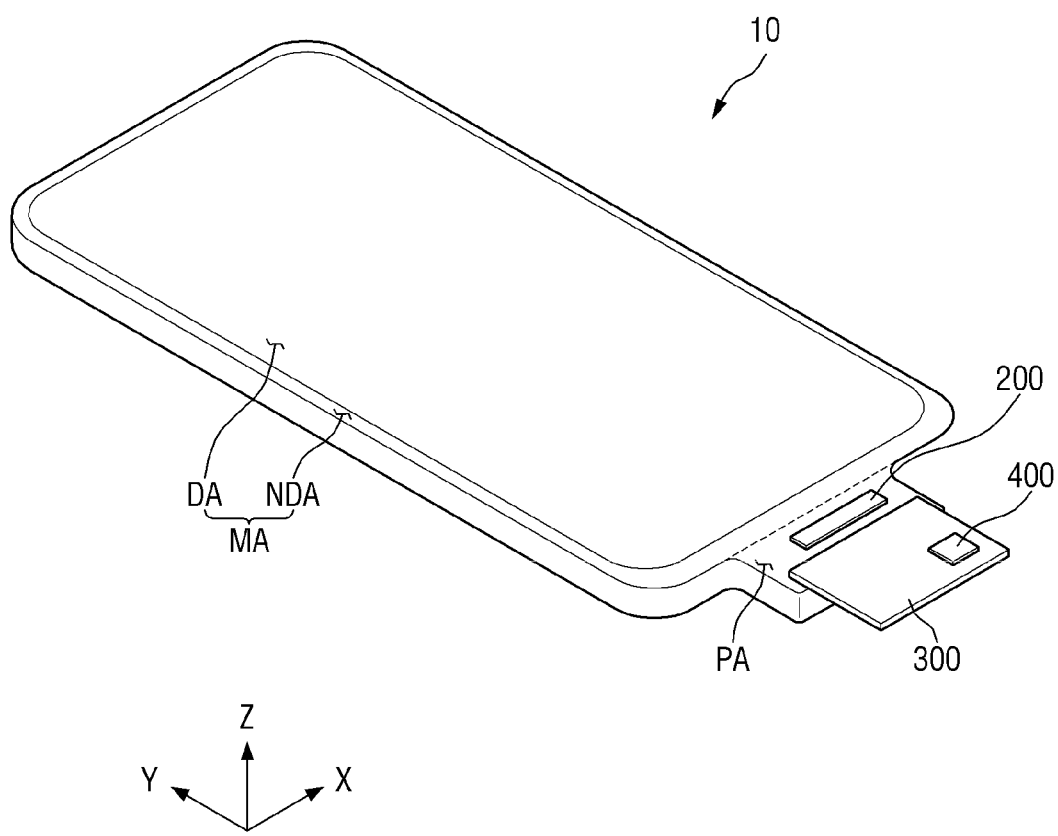
FIG. 1 is a perspective view of a display device according to an embodiment.
Figure 2:
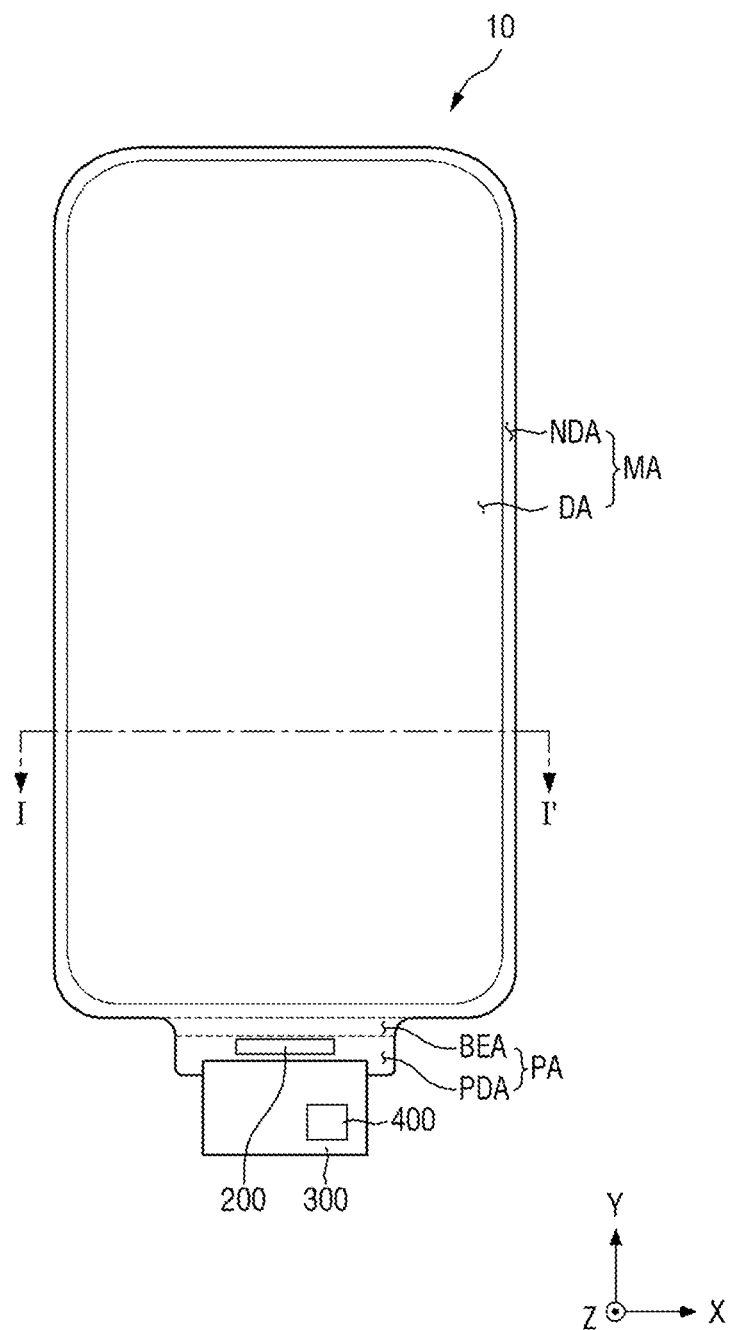
FIG. 2 is a plan view of a display device according to an embodiment.
Figure 3:
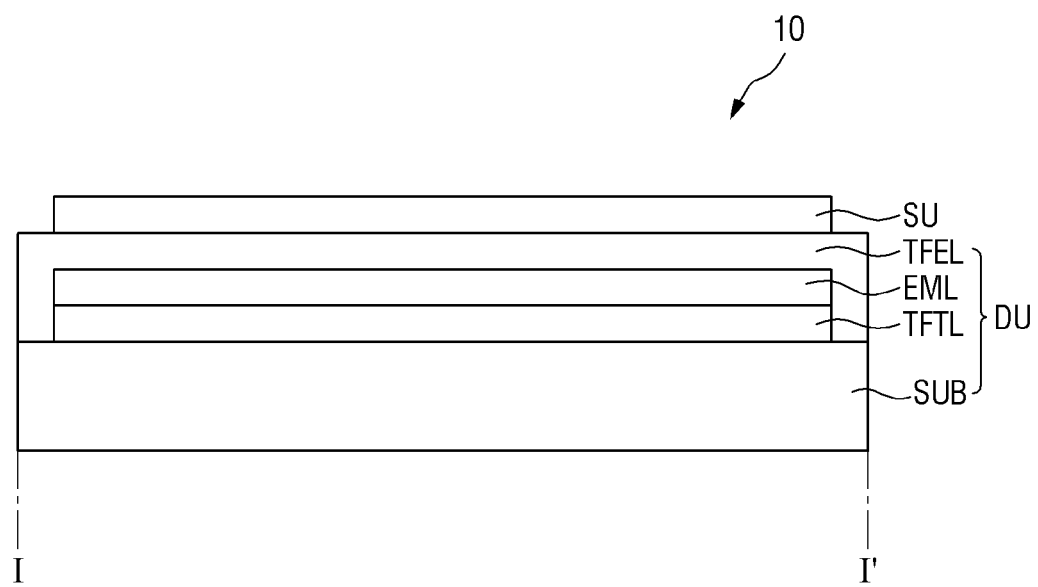
FIG. 3 is a cross-sectional view taken along the line I-I' of FIG. 2 according to an embodiment.

FIG. 1 is a perspective view of a display device 10 according to an embodiment. FIG. 2 is a plan view of the display device 10 according to an embodiment. FIG. 3 is a cross-sectional view taken along the line I-I' of FIG. 2 according to an embodiment.

The display device 10 may display a moving image or a still image. The display device 10 may be used as a display screen for one of various products, such as televisions, notebooks, monitors, billboards, internet-of-things devices, mobile phones, smartphones, tablet computers, smart watches, watch phones, mobile communication terminals, electronic notebooks, electronic books, portable multimedia players (PMPs), navigators, and ultra-mobile PCS (UMPs). The display device 10 may be/include one of an organic light emitting display device, a liquid crystal display device, a plasma display device, a field emission display device, an electrophoretic display device, an electrowetting display device, a quantum dot emission display device, and a micro LED display device. For example, the display device 10 may be/include an organic light emitting display device.

The display device 10 includes a display unit DU (illustrated in FIG. 3), a sensing unit SU (illustrated in FIG. 3), a display driving circuit 200 for driving the display unit DU and the sensing unit SU, a circuit board 300, and a sensing driving unit 400.

The display device 10 may include a main area MA and a protrusion area PA protruding from one side of the main area MA.

The main area MA may have a substantially rectangular shape having short sides in the first direction (X-axis direction) and long sides in the second direction (Y-axis direction). The corner where a short side in the first direction (X-axis direction) meets a long side in the second direction (Y-axis direction) may have a round shape of a predetermined curvature or have a right angle. The display device 10 may have another polygonal shape, circular shape, or elliptical shape. The main area MA may be substantially flat, and may include one or more curved portions. A curved portion may have a constant curvature or a variable curvature.

The main area MA may include a display area DA where pixels are formed to display an image, and a non-display area NDA which is a peripheral area of the display area DA.

In the display area DA, scan lines, data lines, and power supply lines, which are connected to the pixels, may be arranged. When the main area MA includes a curved portion, the display area DA may extend to the curved portion. In this case, displayed images may be seen at the curved portion.

The non-display area NDA may range from the outside of the display area DA to the edge of the main area MA of the display device 10. In the non-display area NDA, a scan driver for applying scan signals to scan lines, and link lines for connecting data lines to a display driving circuit 200 may be arranged.

The protrusion area PA may protrude from one side of the main area MA. For example, the protrusion area PA may protrude from a short side of the main area MA, as shown in FIG. 2. The length of the protrusion area PA in the second direction (Y-axis direction) may be shorter than the length of the main area MA in the first direction (X-axis direction).

The protrusion area PA may include a bending area BEA and a pad area PDA. The pad area PDA may be disposed on one side of the bending area BEA, and the main area MA may be disposed on the other side of the bending area BEA. The display unit DU and the sensing unit SU illustrated in FIG. 3 may be flexible and can be bent, warped, folded, or rolled. Therefore, the display unit DU and the sensing unit SU may be bent from the bending area BEA in a direction opposite to the third direction (Z-axis direction). Thus, the pad area PDA may overlap the main area MA.

The pad area PDA may be provided with pads electrically connected to a display driving circuit 200 and a circuit board 300.

The display driving circuit 200 outputs signals and voltages for driving the display unit DU. For example, the display driving circuit 200 may supply data voltages to data lines. Further, the display driving circuit 200 may supply a power supply voltage to a power supply line, and may supply scan control signals to a scan driver. The display driving circuit 200 may be formed as an integrated circuit (IC), and may be mounted on the display unit DU in the pad area PDA by a chip on glass (COG) method, a chip on plastic (COP) method. The display driving circuit 200 may be mounted on the circuit board 300.

The pads may include display pads electrically connected to the display driving circuit 200 and sensing pads electrically connected to the lines included in the sensing unit SU.

The circuit board 300 may be attached onto the pads using an anisotropic conductive film. Thus, the lead lines of the circuit board 300 may be electrically connected to the pads. The circuit board 300 may be a flexible printed circuit board, a printed circuit board, or a flexible film such as a chip on film.

The sensing driving circuit 400 may be connected to the electrodes of the sensing unit SU as shown in FIG. 3. The sensing driving circuit 400 applies driving signals to the electrodes of the sensing unit SU and measures capacitance values of the electrodes. The driving signal may be a signal having a plurality of driving pulses. The sensing driving circuit 400 may determine a touch input, a pressure, a heart rate, and the like according to capacitance values.

The sensing driving circuit 400 may be disposed on the circuit board 300. The sensing driving circuit 400 may be formed as an integrated circuit (IC) and may be mounted on the circuit board 300.

Referring to FIG. 3, the display device 10 may include a display unit DU. The display unit DU may include a substrate SUB and may include a thin film transistor layer TFTL, a light emitting element layer EML, and a thin film encapsulation layer TFEL, which are sequentially disposed on the substrate SUB. The display device 10 may further include a sensing unit SU disposed on the display unit DU.

The substrate SUB may include an insulating material such as glass, quartz, or a polymer resin. Examples of the polymer resin may include polyethersulphone (PES), polyacrylate (PA), polyarylate (PAR), polyetherimide (PEI), polyethylene napthalate (PEN), polyethylene terepthalate (PET), polyphenylene sulfide (PPS), polyallylate, polyimide (PI), polycarbonate (PC), cellulose triacetate (CAT), cellulose acetate propionate (CAP), and combinations of some of the above. Alternatively or additionally, the substrate SUB may include a metal material.

The substrate SUB may be a rigid substrate or a flexible substrate capable of bending, folding, rolling, and the like. When the substrate SUB is a flexible substrate, it may be formed of polyimide (PI).

Figure 4:
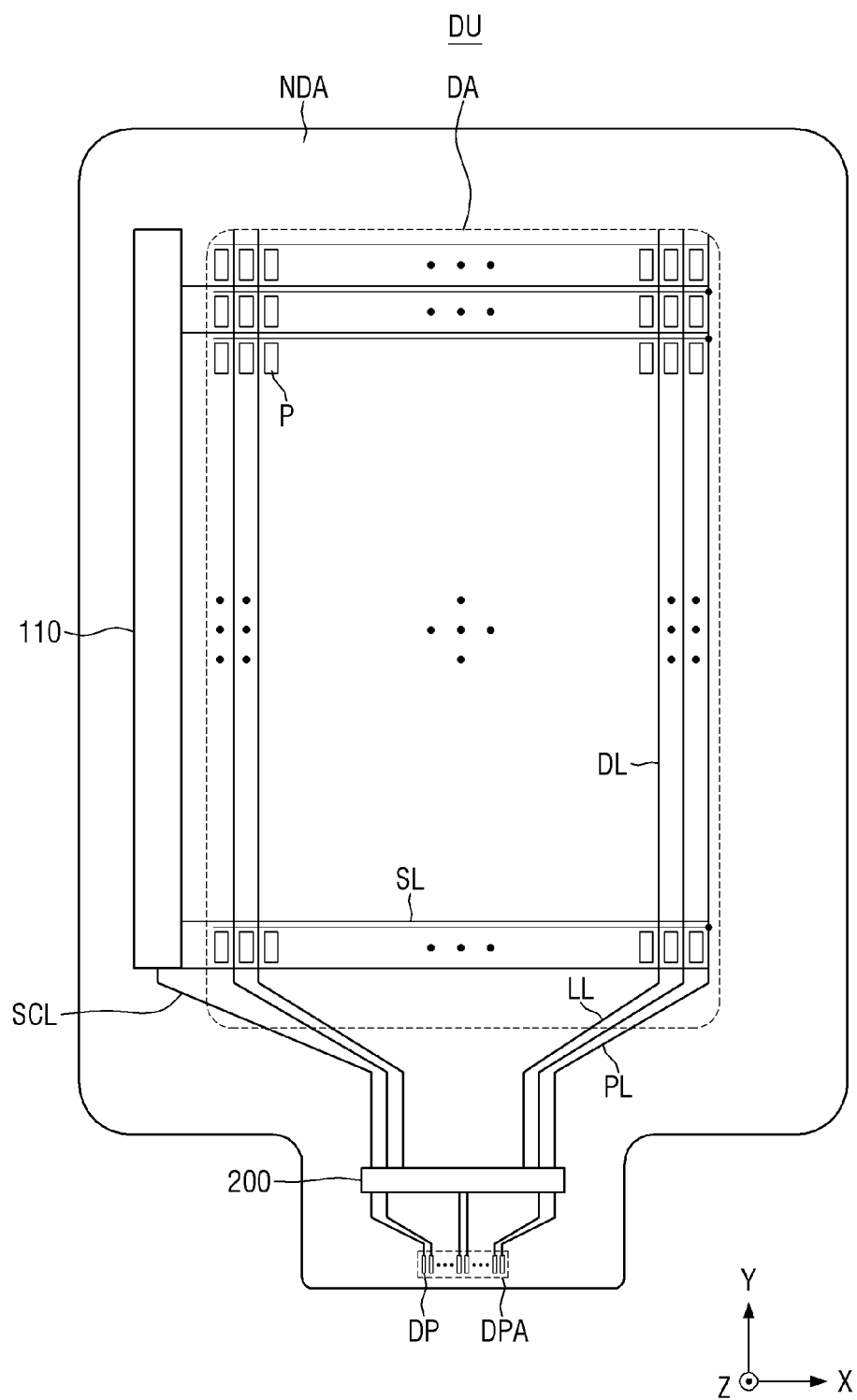
FIG. 4 is a plan view of the display unit of FIG. 3 according to an embodiment.

The thin film transistor layer TFTL may be disposed on the substrate SUB. The thin film transistor layer TFTL may be provided with not only thin film transistors of each pixel but also scan lines, data lines, power supply lines, scan control lines, and routing lines for connecting pads and data lines. Each of the thin film transistors may include a gate electrode, a semiconductor layer, a source electrode, and a drain electrode. When a scan driver 110 is formed in the non-display area NDA as shown in FIG. 4, the scan driver 110 may include thin film transistors.

The thin film transistor layer TFTL may be disposed in the display area DA and the non-display area NDA. Specifically, thin film transistors, scan lines, data lines and power supply lines corresponding to pixels of the thin film transistor layer TFTL may be disposed in the display area DA. Further, scan control lines and link lines of the thin film transistor layer TFTL may be disposed in the non-display area NDA.

The light emitting element layer EML may be disposed on the thin film transistor layer TFTL. The light emitting element layer EML may include pixels each including a first electrode, a light emitting layer, and a second electrode, and a pixel defining film defining the pixels. The light emitting layer may be an organic light emitting layer including an organic material. The light emitting layer may include a hole transporting layer, an organic light emitting layer, and an electron transporting layer. When a predetermined voltage is applied to the first electrode through the thin film transistor of the thin film transistor layer TFTL and a cathode voltage is applied to the second electrode, holes and electrons are transferred to the organic light emitting layer through the hole transporting layer and the electron transporting layer, respectively, and are combined with each other to emit light. The pixels of the light emitting element layer EML may be arranged in the display area DA.

The thin film encapsulation layer TFEL may be disposed on the light emitting element layer EML. The thin film encapsulation layer TFEL serves to prevent oxygen or moisture from penetrating into the light emitting element layer EML. For this purpose, the thin film encapsulation layer TFEL may include at least one inorganic film. The inorganic film may be a silicon nitride layer, a silicon oxynitride layer, a silicon oxide layer, a titanium oxide layer, or an aluminum oxide layer. Further, the thin film encapsulation layer TFEL serves to protect the light emitting element layer EML from foreign matter such as dust. For this purpose, the thin film encapsulation layer TFEL may include at least one organic film. The organic film may include an acrylic resin, an epoxy resin, a phenolic resin, a polyamide resin, or a polyimide resin.

The thin film encapsulation layer TFEL may be disposed in both the display area DA and the non-display area NDA. Specifically, the thin film encapsulation layer TFEL may be disposed to cover the light emitting element layer EML in the display area DA and the non-display area NDA and cover the thin film transistor layer TFTL in the non-display area NDA.

The sensing unit SU may be disposed on the thin film encapsulation layer TFEL. When the sensing unit SU is disposed directly on the thin film encapsulation layer TFEL, the thickness of the display device 10 may be advantageously reduced, compared to a separate sensing panel including the sensing unit SU attached onto the thin film encapsulation layer TFEL.

The sensing unit SU may include electrodes for sensing a user's touch, a touch pressure, a heart rate and the like by a capacitance method, and lines for connecting the electrodes and the pads. For example, the sensing unit SU may sense a user's touch by a self-capacitance method or a mutual capacitance method.

Figure 5:
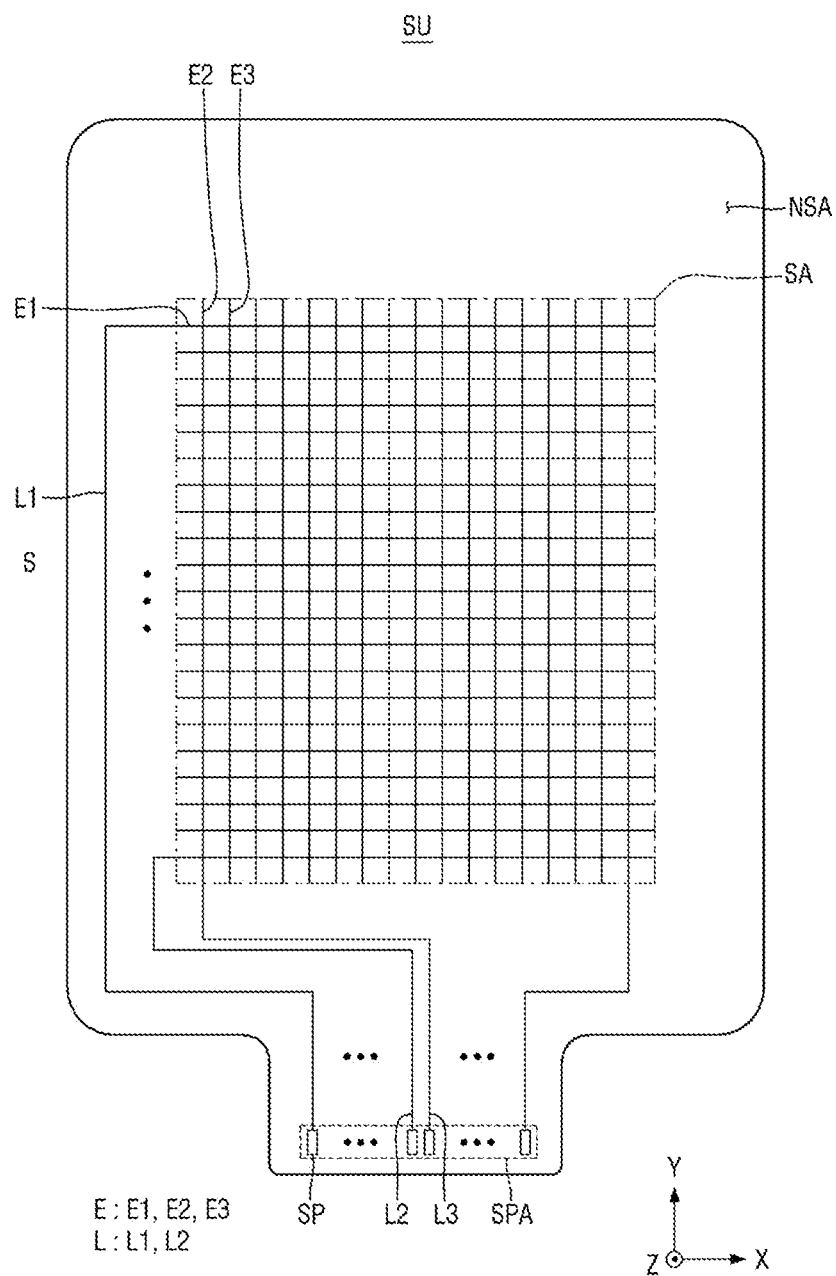
FIG. 5 is a plan view of the sensing unit of FIG. 3 according to an embodiment.

The electrodes of the sensing unit SU may be arranged in the sensing area SA overlapping the display area DA as shown in FIG. 5. The lines of the sensing unit SU may be arranged in a non-sensing area NSA overlapping the non-display area NDA as shown in FIG. 5.

Although not shown in the drawing, a protective layer may be disposed on the sensing unit SU. The protective layer may include, for example, a window member. The protective layer may be attached to the sensing unit SU by an optically clear adhesive (OCA) or the like. Further, in some embodiments, the display device 10 may further include an optical member. For example, an optical member (such as a polarization film) may be interposed between the sensing unit SU and the protective layer. In some embodiments, a refractive index matching layer may be disposed between the sensing unit SU and the protective layer.

FIG. 4 is a plan view showing the display unit of FIG. 3 according to an embodiment.

For illustration, FIG. 4 shows a display unit DU including pixels P, scan lines SL, data lines DL, power supply lines PL, scan control lines SCL, a scan driver 110, a display driving circuit 200, and display pads DP.

Referring to FIG. 4, the display unit DU may include the display area DA and the non-display area NDA.

The scan lines SL, the data lines DL, the power supply lines PL, and the pixels P are arranged in the display area DA. The scan lines SL may be lengthwise in a first direction (X-axis direction) in parallel, and the data lines DL may be lengthwise in a second direction (Y-axis direction) different from (e.g., perpendicular to) the first direction (X-axis direction). The power supply lines PL may include at least one line disposed parallel to the data lines DL and a plurality of lines branched from the at least one line in and being lengthwise the first direction (X-axis direction).

Each of the pixels P may be connected to at least one of the scan lines SL, one of the data lines DL, and the power supply line PL. Each of the pixels P may include thin film transistors including a driving transistor and at least one switching transistor, an organic light emitting diode, and a capacitor. When a pixel P receives a scan signal from the corresponding scan line SL, it may receive a data voltage from the corresponding data line DL, and may supply a driving current to the corresponding organic light emitting diode to emit light.

The scan driver 110 is connected to the display driving circuit 200 through at least one scan control line SCL. Therefore, the scan driver 110 may receive a scan control signal from the display driving circuit 200. The scan driver 110 may generate scan signals according to the scan control signal, and may supply the scan signals to the scan lines SL.

FIG. 4 illustrates that the scan driver 110 in the non-display area NDA located at the left outside of the display area DA. Scan drivers may be disposed in the non-display area NDA located at the left and right outsides of the display area DA.

The display driving circuit 200 is connected to the display pads DP arranged in the display pad area DPA to receive digital video data and timing signals. The display driving circuit 200 converts digital video data into analog positive/negative data voltages and supplies the analog positive/negative data voltages to the data lines DL through the link lines LL. The display driving circuit 200 generates and supplies a scan control signal for controlling the scan driver 110 through the scan control line SCL. The pixels P to which data voltages will be supplied are selected by the scan signals of the scan driver 110, and the data voltages are supplied to the selected pixels P. The display driving circuit 200 may be an integrated circuit (IC), and may be attached onto the substrate SUB by a chip on glass (COG) method, a chip on plastic method, or an ultrasonic bonding method.

FIG. 5 is a plan view showing the sensing unit of FIG. 3 according to an embodiment.

Referring to FIG. 5, the sensing unit SU includes a sensing area SA for sensing a user's touch input, touch pressure, and heart rate, and includes a non-sensing area NSA disposed around the sensing area SA. The sensing area SA may overlap the display area DA of the display unit DU, and the non-sensing area NSA may overlap the non-display area NDA of the display unit DU.

In some embodiments, the sensing area SA may be divided according to the user's touch input, touch pressure, and heart rate. For example, the touch input may be detected at the front of the sensing area SA, but the touch pressure and the heart rate may be detected only in a part of the sensing area SA. In some embodiments, in the sensing area SA, biometric information other than the heart rate may be recognized. For example, skin moisture may be detected.

Electrodes E may be arranged in the sensing area SA. The electrodes E may include first electrodes E1 (or first-type electrodes E1), second electrodes E2 (or second-type electrodes E2), and third electrodes E3 (or third-type electrodes E3). The first electrodes E1 may be sensing electrodes, the second electrodes E2 may be driving electrodes, and the third electrodes E3 may be electrodes that are (switched to) driving electrodes or sensing electrodes according to a mode.

The first electrodes E1 and the second electrodes E2 may be arranged on different layers. For example, the first electrodes E1 may be insulated from the second electrodes E2 by an insulating layer disposed between the first electrodes E1 and the second electrodes E2. The third electrodes E3 may be arranged on the same layer (i.e., directly disposed on the same face of the insulating layer) as the second electrodes E2.

The first electrodes E1 may extend in the first direction (X-axis direction) individually, and may be spaced apart from each other in the second direction (Y-axis direction). The second electrodes E2 and the third electrodes E3 may extend in the second direction (Y-axis direction) individually, and may be spaced apart from each other in the first direction (X-axis direction).

The second electrodes E2 and the third electrodes E3 may be alternately arranged, the first electrodes E1 may intersect the second electrodes E2 in a plan view of the sensing unit SU, and the first electrodes E1 may intersect the third electrodes E3 in the plan view of the sensing unit SU.

Each of the first electrodes E1, the second electrodes E2, and the third electrodes E3 may include or may be (made of) silver (Ag) nanowires, metal mesh, carbon nanotubes (CNTs), or a polymer material. Each of the first electrodes E1, the second electrodes E2, and the third electrodes E3 may be made of one or more materials having high light transmittance and low specific resistance.

Lines L may be arranged in the non-sensing area NSA. For example, the lines L may include first(-type) lines L1, second(-type) lines L2, and third(-type) lines L3. The first lines L1 may be electrically connected to the first electrodes E1, the second lines L2 may be electrically connected to the second electrodes E2, and the third lines L3 may be electrically connected to the third electrodes E3. One end of a first line L1 may be connected to a first electrode E1, and the other end of the first line L1 may be connected to a sensing pad SP disposed in the sensing pad area SPA. One end of a second line L2 may be connected to a second electrode E2, and the other end of the second line L2 may be connected to a sensing pad SP. One end of a third line L3 may be connected to a third electrode E3, and the other end of the third line L3 may be connected to a sensing pad SP.

Figure 6:
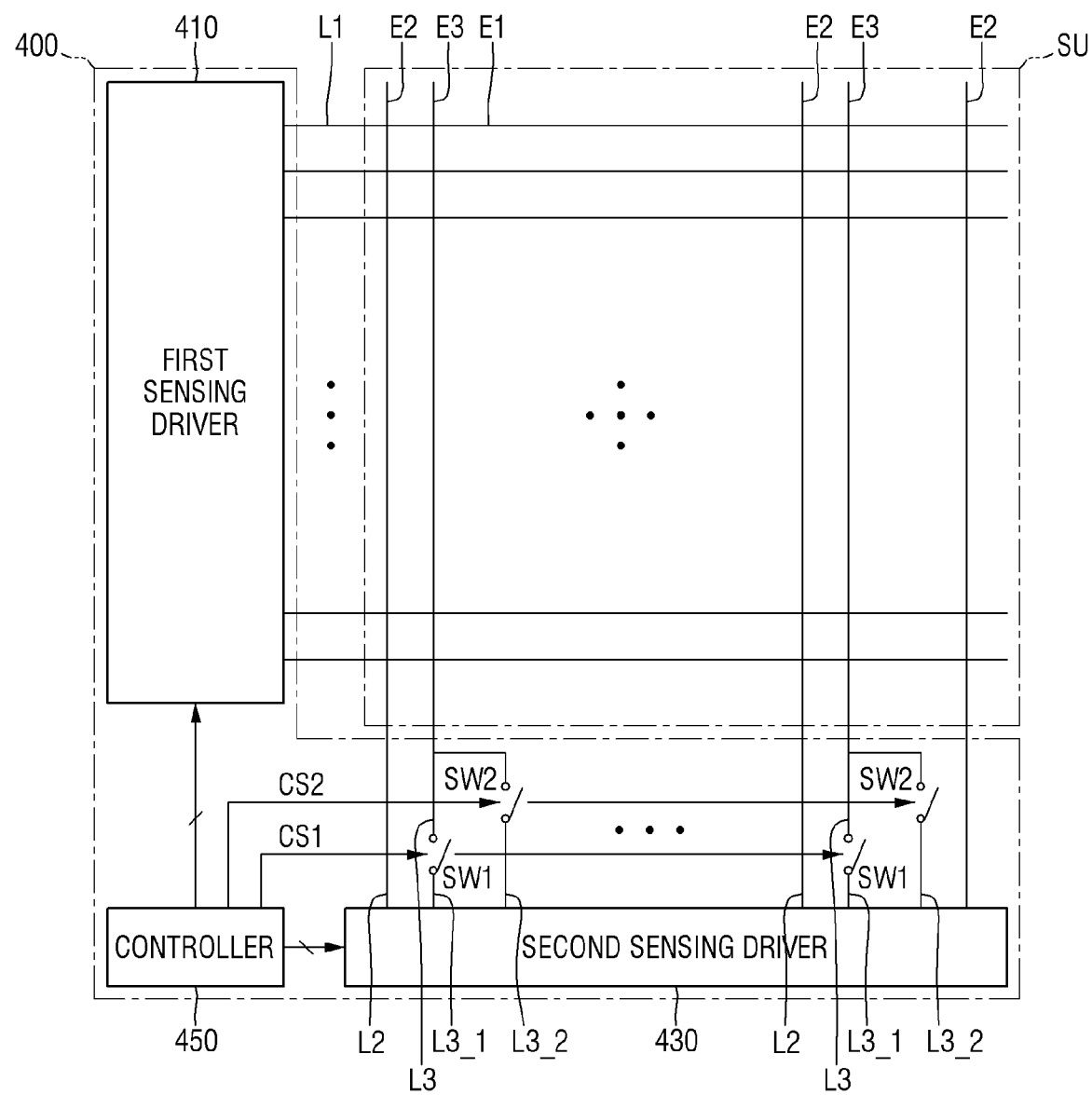
FIG. 6 is a block diagram schematically illustrating a sensing driving circuit according to an embodiment.

FIG. 6 is a block diagram illustrating a sensing driving circuit according to an embodiment.

Referring to FIG. 6, the sensing driving circuit 400 may include a first sensing driver 410, a second sensing driver 430, and a controller 450. The first sensing driver 410, the second sensing driver 430, and the controller 450 may be integrated in one read-out integrated circuit (ROIC).

The first lines L1 connected to the first electrodes E1 may be connected to the first sensing driver 410, the second lines L2 connected to the second electrodes E2 may be connected to the second sensing driver 430, and the third lines L3 connected to the third electrodes E3 may be connected to the second sensing driver 430 through switches.

A first switch SW1 (or first-type switch SW1) and a second switch SW2 (or second-type switch SW2) may be disposed between each third line L3 and the second sensing driver 430, and the third line L3 may be connected to a corresponding third-first(-type) line L3-1 and a corresponding third-second(-type) line L3-2. For example, the third line L3 may be connected to the third-first line L3-1 through the first switch SW1, and the third line L3 may be connected to the third-second line L3-2 through the second switch SW2. Transistors may be provided as or instead of the first switch SW1 and the second switch SW2.

Sensing signals may be received from the first lines L1, driving signals may be applied to the second lines L2, driving signals may be applied to the third-first lines L3-1, and sensing signals may be received from the third-second lines L3-2.

Specifically, the first sensing driver 410 may select the first lines L1 to receive sensing signals under the control of the controller 450, and may detect capacitance changes of electrodes based on the sensing signals received through the selected first lines L1.

The second sensing driver 430 may select the second lines L2 to output driving signals under the control of the controller 450, and may supply the driving signals to the selected second lines L2. The second sensing driver 430 may sequentially provide the driving signals to the second lines L2.

The second sensing driver 430 may select the third-first lines L3-1 to output driving signals under the control of the controller 450, and may supply the driving signals to the selected third-first lines L3-1. The second sensing driver 430 may sequentially provide the driving signals to the third-first lines L3-1.

The second sensing driver 430 may select the third-second lines L3-2 to receive sensing signals under the control of the controller 450, and may detect capacitance changes of electrodes based on sensing signals received through the selected third-second lines L3-2.

The controller 450 may transmit (copies/instances of) a first control signal CS1 to the first switches SW1 to connect the third lines L3 to the third-first lines L3-1, respectively, or may transmit (copies/instances of) a second control signal CS2 to the second switches SW2 to connect the third lines L3 to the third-second lines L3-2, respectively. When the first control signal CS1 is output from the controller 450, driving signals transmitted by the third-first lines L3-1 may be provided to the third lines L3. When the second control signal CS2 is output from the controller 450, the third lines L3 may be connected to the third-second lines L3-2 to receive sensing signals.

FIG. 6 illustrates that the sensing driving circuit 400 and the sensing unit SU are separate components. The sensing driving circuit 400 may be a component included in the sensing unit SU.

The third electrodes E3 connected to the third lines L3 may be driven as sensing electrodes or driving electrodes according to a mode of the sensing unit SU. The sensing unit SU may sense a touch input, a touch pressure, and a heart rate.

Figure 7:
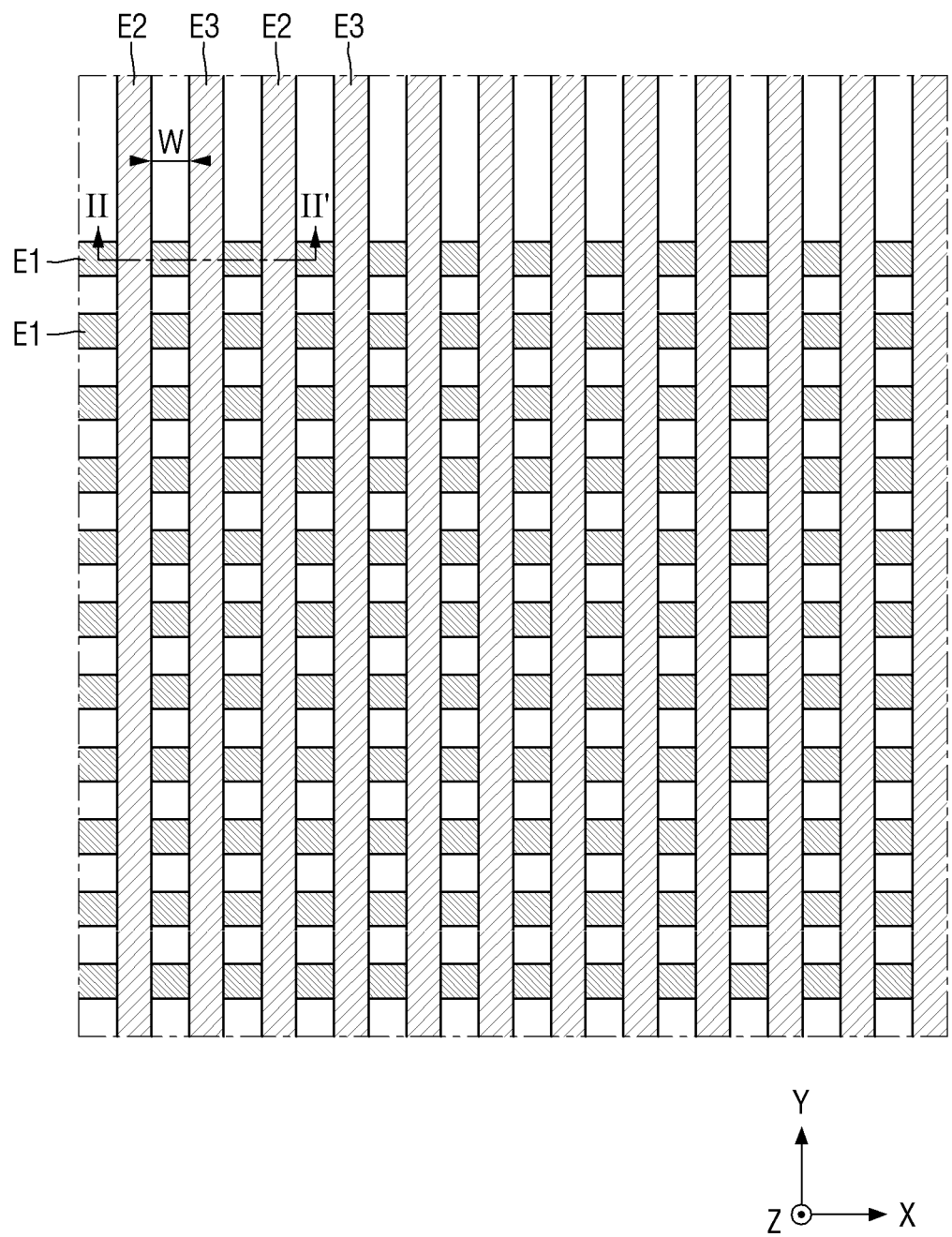
FIG. 7 is a plan view schematically illustrating a first electrode, a second electrode, and a third electrode of the sensing unit according to an embodiment.
Figure 8:
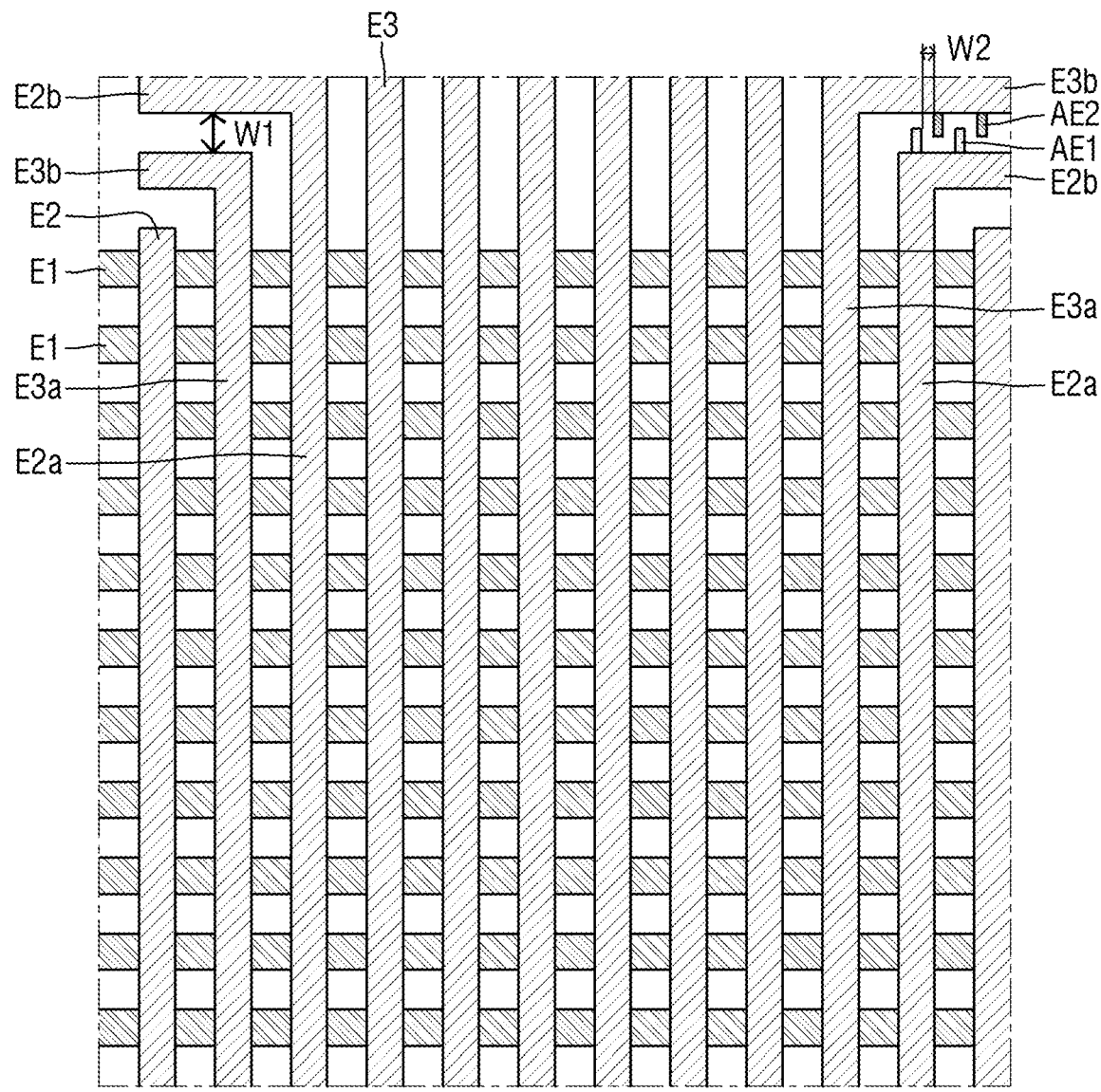
FIG. 8 is a plan view schematically illustrating a first electrode, a second electrode, and a third electrode of the sensing unit according to an embodiment.
Figure 9:
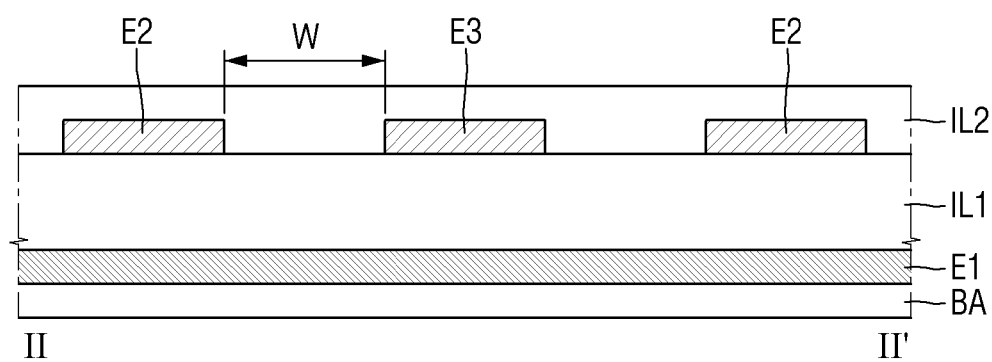
FIG. 9 is a cross-sectional view taken along the line II-II' of FIG. 7 according to an embodiment.

FIG. 7 is a plan view schematically illustrating first electrodes, second electrodes, and third electrodes of the sensing unit SU according to an embodiment. FIG. 8 is a plan view schematically illustrating first electrodes, second electrodes, and third electrodes of the sensing unit SU according to an embodiment. FIG. 9 is a cross-sectional view taken along the line II-II' of FIG. 7.

Referring to FIG. 7, the first electrodes E1 may intersect the second electrodes E2 and may intersect the third electrodes E3. The first electrodes E1 may extend individually in the first direction (X-axis direction), and may be spaced apart from each other in the second direction (Y-axis direction). The second electrodes E1 and the third electrodes E3 may extend individually in the second direction (Y-axis direction), and may be spaced apart from each other in the first direction (X-axis direction).

The second electrodes E2 and the third electrodes E3 may be alternately arranged. The second electrodes E2 and the third electrodes E3 may be spaced apart from each other in the first direction (X-axis direction), and The distance W between a second electrode E2 and an immediately neighboring third electrodes E3 may be in a range of 2 mm to 4 mm. The distance W may be configured according to the components laminated on the second electrode E2 and the third electrode E3. According to a driving mode, the sensing unit SU may measure the touch input and the touch pressure through changes in the capacitance formed in the vertical direction (or Z-axis direction) among the first electrodes E1, the second electrodes E2, and the third electrodes E3. Further, according to the driving mode, the sensing unit SU may measure a heart rate through a change in fringe capacitance formed by a fringe field between the second electrodes E2 and the third electrodes E3.

Referring to FIG. 8, a second electrode E2_1 may include a first portion E2a and a second portion E2b, and a third electrode E3_1 may include a first portion E3a and a second portion E3b. For example, the first portion E2a may extend in the second direction (Y-axis direction), and the second portion E2b may be bent from the first portion E2a. The first portion E3a may extend in the second direction (Y-axis direction), and the second portion E3b may be bent from the first portion E3a. The bending direction of the second electrode E2_1 may be the same as the bending direction of the third electrode E3_1, and the second portion E2b of the second electrode E2_1 and the second portion E3b of the third electrode E3_1 may have a first spacing distance W1.

The sensing unit SU may include first(-type) auxiliary electrodes AE1 and second(-type) auxiliary electrodes AE2. For example, the first auxiliary electrodes AE1 may protrude from one side of the second portion E2b of the second electrode E2_1, and the second auxiliary electrodes AE2 may protrude from one side of the second portion E3b of the third electrode E3_1 facing the second portion E2b of the second electrode E2_1. The first auxiliary electrodes AE1 and the second auxiliary electrodes AE2 may be alternately arranged. A first auxiliary electrode AE1 and an immediately neighboring second auxiliary electrode AE2 may have a second spacing distance W2. The first auxiliary electrodes AE1 may be in contact with the second portion E2b of the second electrode E2_1, and the second auxiliary electrode AE2 may be in contact with the second portion E3b of the third electrode E3_1.

The second spacing distance W2 may be smaller than the first spacing distance W1. For example, the first spacing distance W1 may be in a range of 2 mm to 4 mm, and the second spacing distance W2 may be in a range of 10 um and 500 um. The first auxiliary electrodes AE1 and the second auxiliary electrode AE2 may be used to measure skin moisture. For example, the sensing unit SU may measure skin moisture through a change in fringe capacitance formed by a fringe field between the first auxiliary electrodes AE1 and the second auxiliary electrodes AE2.

Referring to FIG. 9, the sensing unit SU may include a base BA, a first electrode E1, a first insulating layer IL1, second electrodes E2, third electrodes E3, and a second insulating layer IL2.

The base BA may be a multi-layer film in which two or more inorganic layers, including a silicon nitride layer, a silicon oxynitride layer, a silicon oxide layer, a titanium oxide layer, and an aluminum oxide layer, are laminated. The base BA may be disposed on the thin film encapsulation layer TFEL shown in FIG. 3, such that the thin film encapsulation layer TFEL may be positioned between the base BA and the thin film transistor layer TFTL.

The first electrode E1 may be disposed on the base BA. The first electrode E1 may include or may be (made of) Ag nanowires, metal mesh, carbon nanotubes (CNTs), or a polymer material. The first electrode E1 may be made of one or more materials having high light transmittance and low specific resistance.

The first insulating layer IL1 may be disposed on the first electrode E1. For example, the first insulating layer IL1 may be in contact with the first electrode E1 and portions of the base BA exposed between the first electrode E1. The first insulating layer IL1 may include polydimethylsiloxane (PDMS). The first insulating layer IL1 may include one or more materials that are transparent and stretchable.

The second electrodes E2 and the third electrodes E3 may be disposed on the first insulating layer IL1. The second electrodes E2 and the third electrodes E3 may be alternately arranged and may be spaced apart from each other.

The second electrodes E2 and the third electrodes E3 may be made of the same material as the first electrode E1. The second insulating layer IL2 is disposed on the second electrodes E2 and the third electrodes E3. The second insulating layer IL2 may be in contact with the second electrodes E2 and the third electrode E3. The second insulating layer IL2 may be in contact with portions of the first insulating layer IL1 exposed between the second electrodes E2 and the third electrodes E3. The second insulating layer IL2 may be made of the same material as the first insulating layer IL1. For example, the second insulating layer IL2 may include polydimethylsiloxane (PDMS). The second insulating layer IL2 may include one or more materials that are transparent and stretchable. The first electrode E1, the second electrodes E2, and the third electrodes E3 may be insulated from each other by the first insulating layer IL1 and the second insulating layer IL2.

Figure 10:
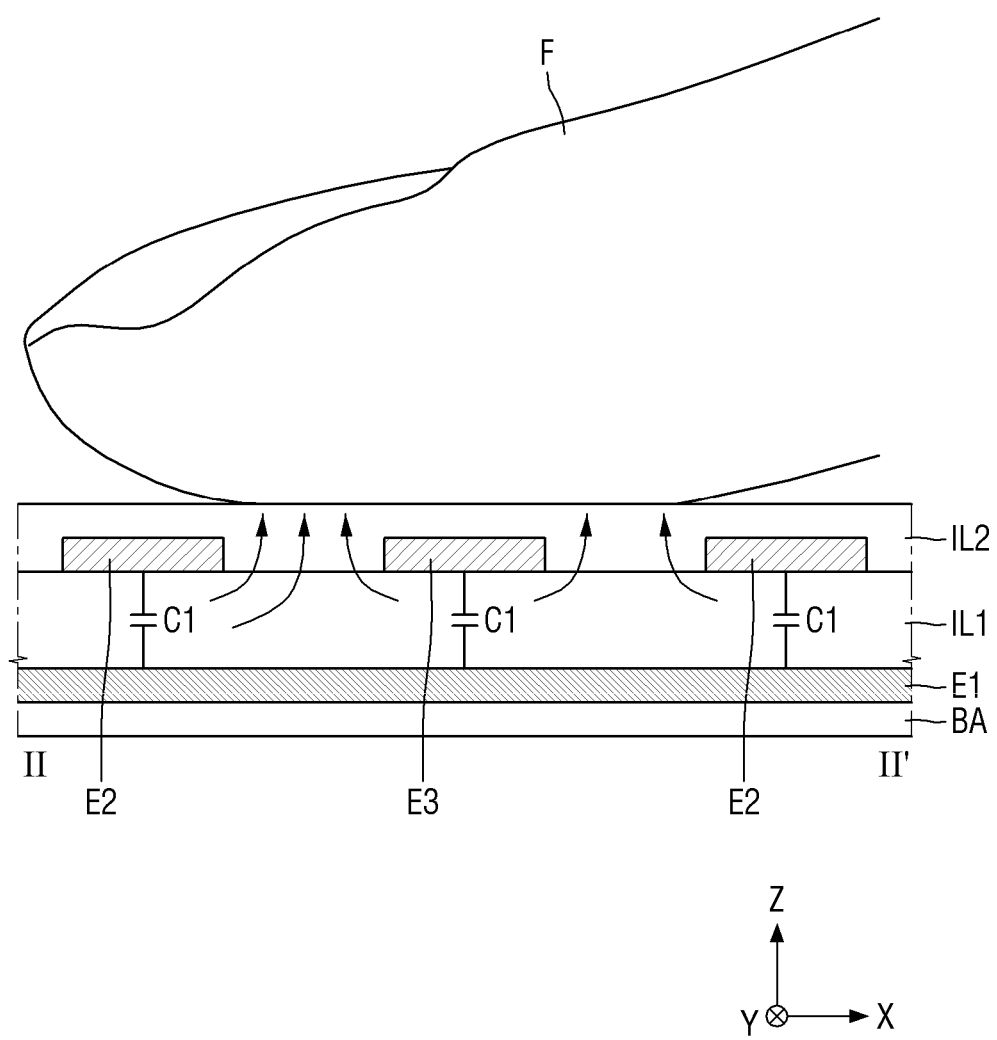
FIG. 10 is a view schematically illustrating a touch input state according to an embodiment.
Figure 11:
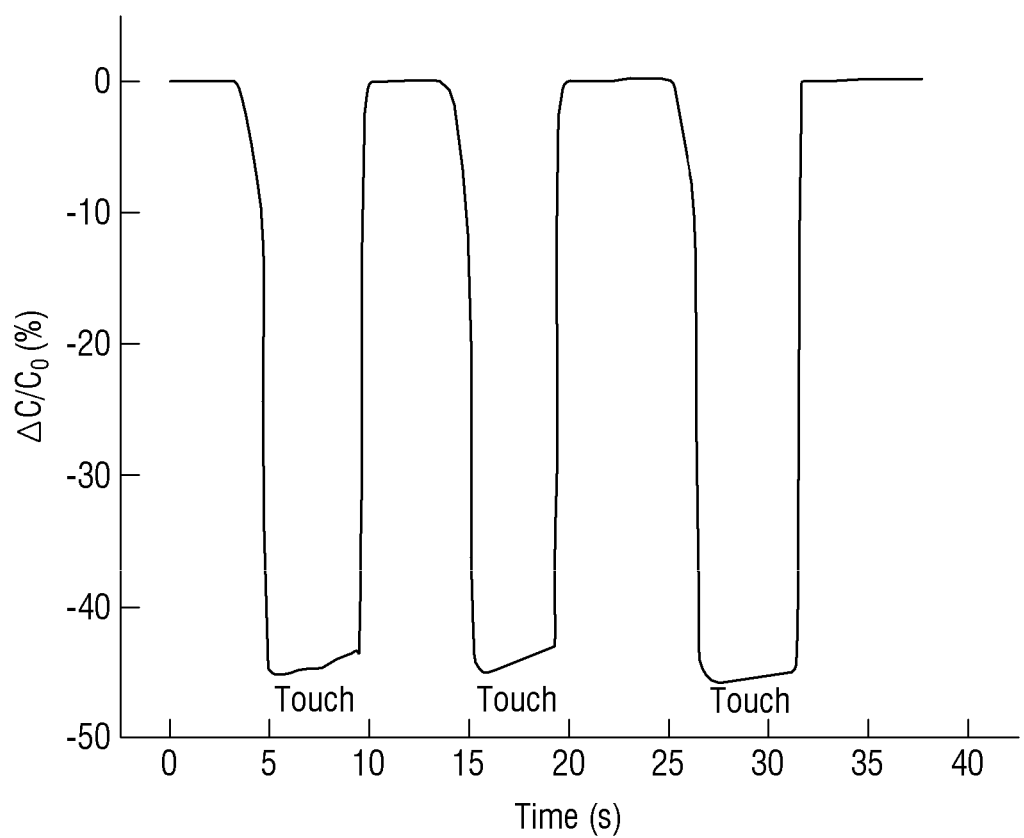
FIG. 11 is a graph illustrating the change in a first capacitance when a touch is input according to an embodiment.
Figure 12:
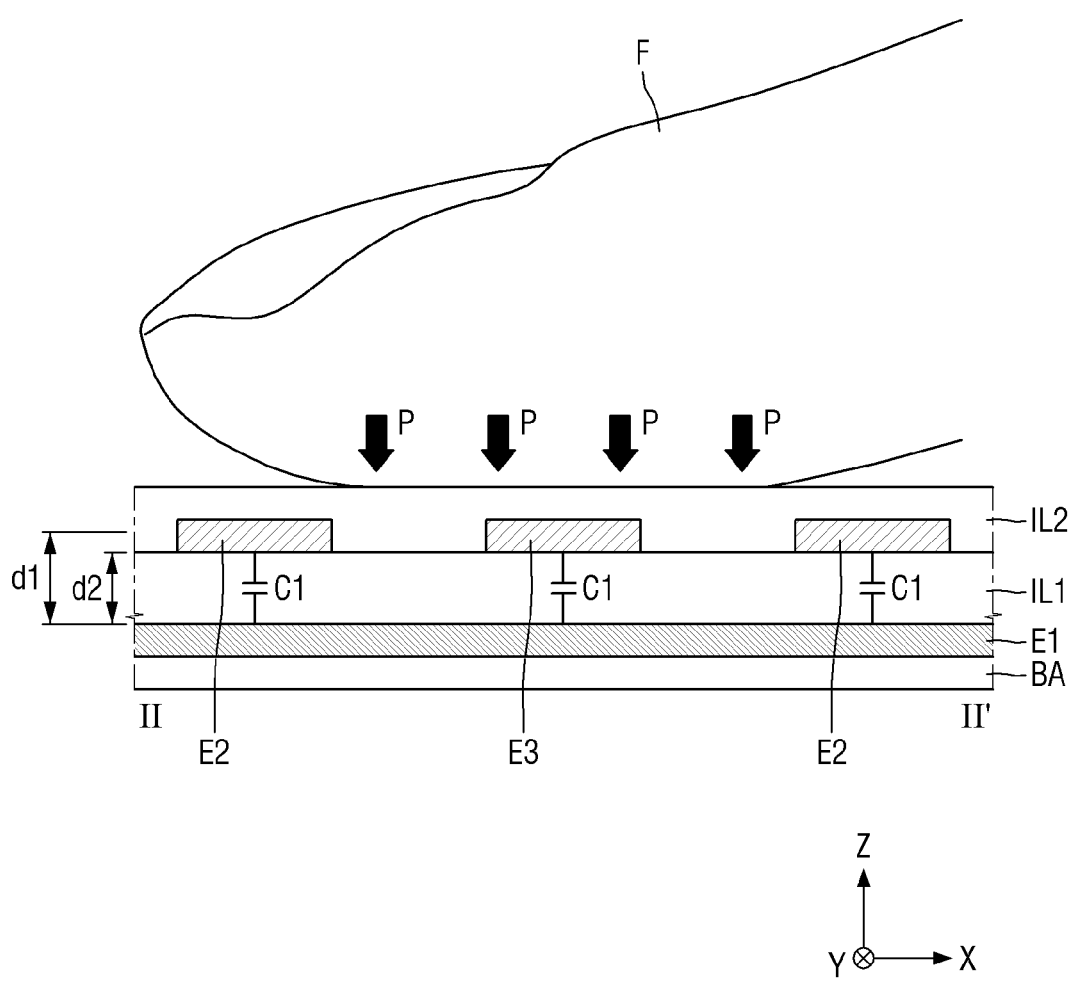
FIG. 12 is a view schematically illustrating a touch input state according to an embodiment.
Figure 13:
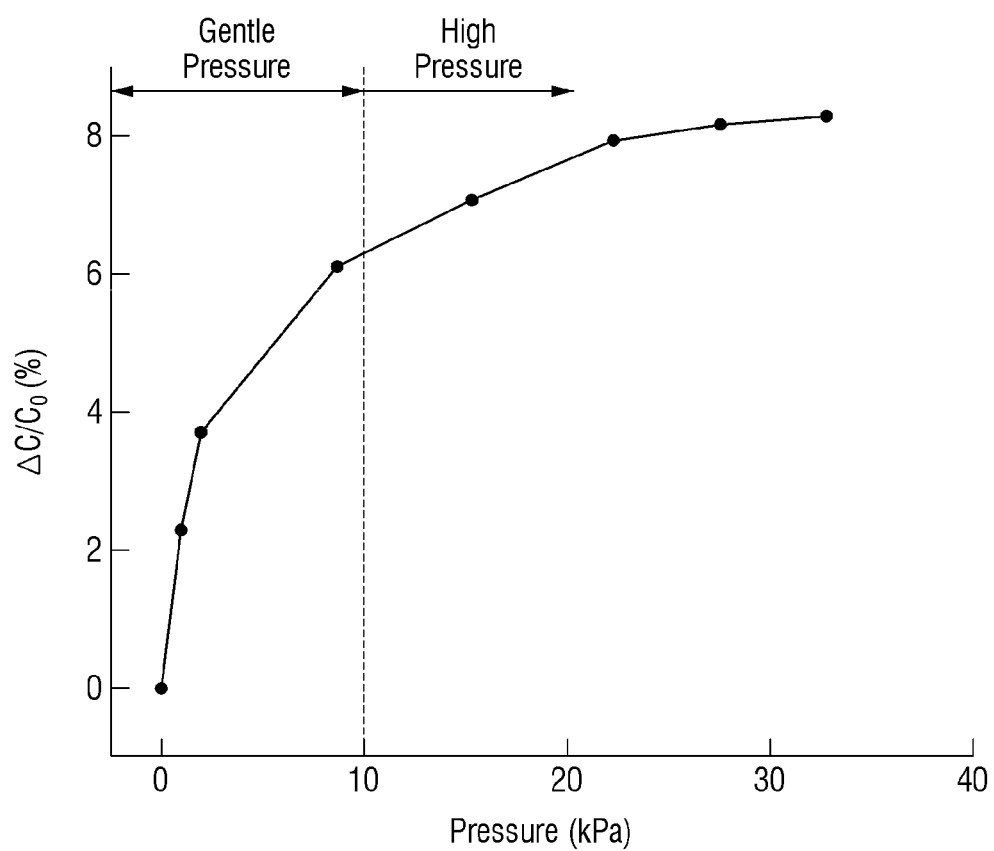
FIG. 13 is a graph illustrating the change in a first capacitance when a touch is input according to an embodiment.
Figure 14:
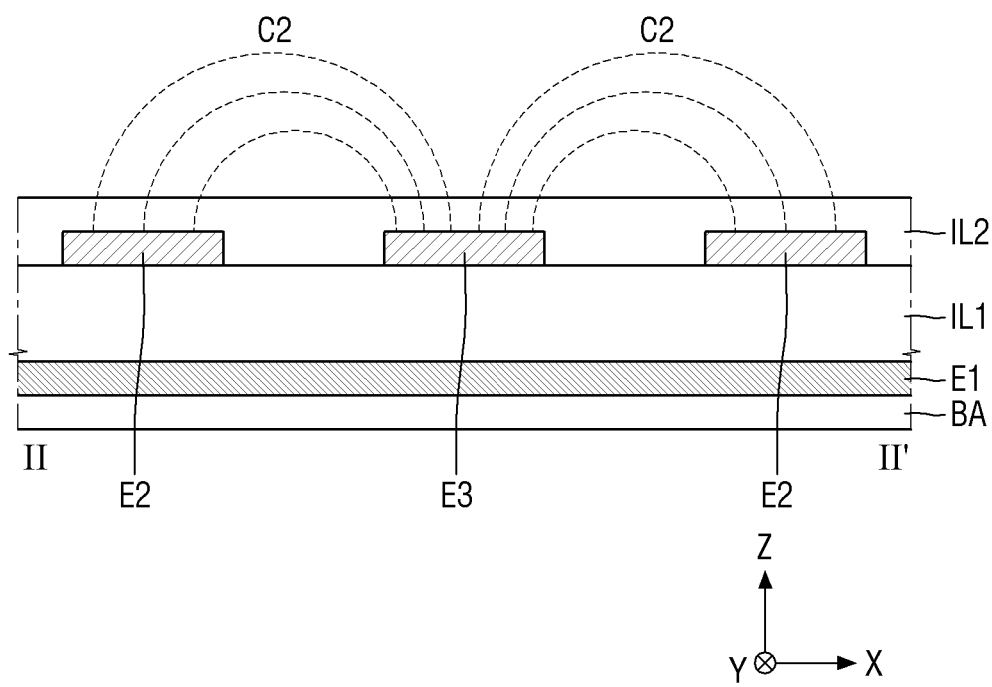
FIG. 14 is a view schematically illustrating the formation of a second capacitance according to an embodiment.
Figure 15:
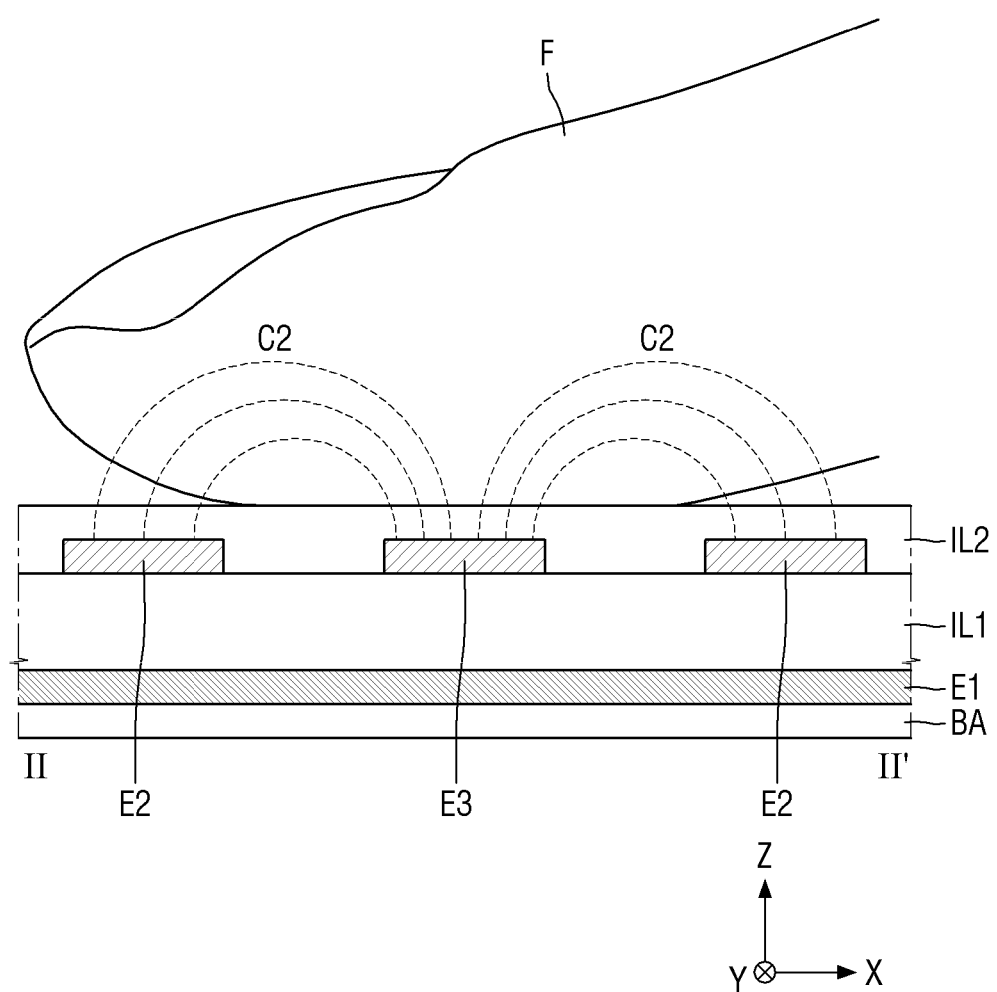
FIG. 15 is a view schematically illustrating the state of sensing a heart rate according to an embodiment.
Figure 16:
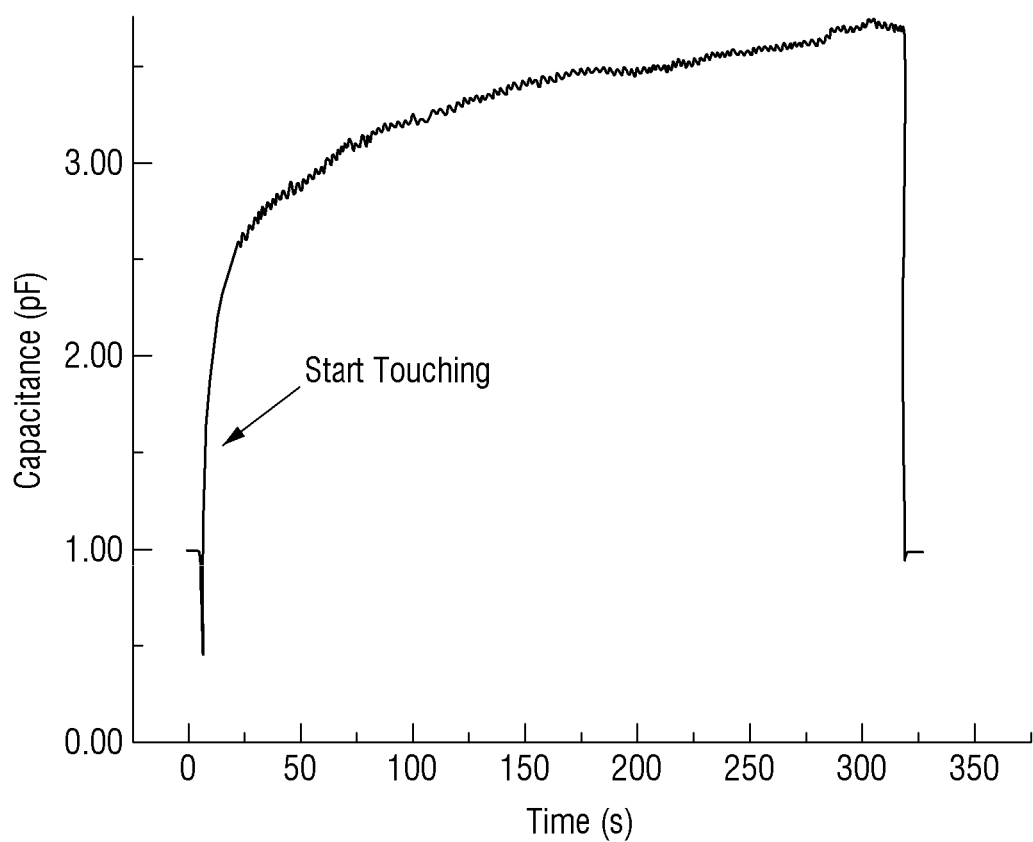
FIG. 16 is a graph illustrating the change in a second capacitance when a heart rate is detected according to an embodiment.
Figure 17:
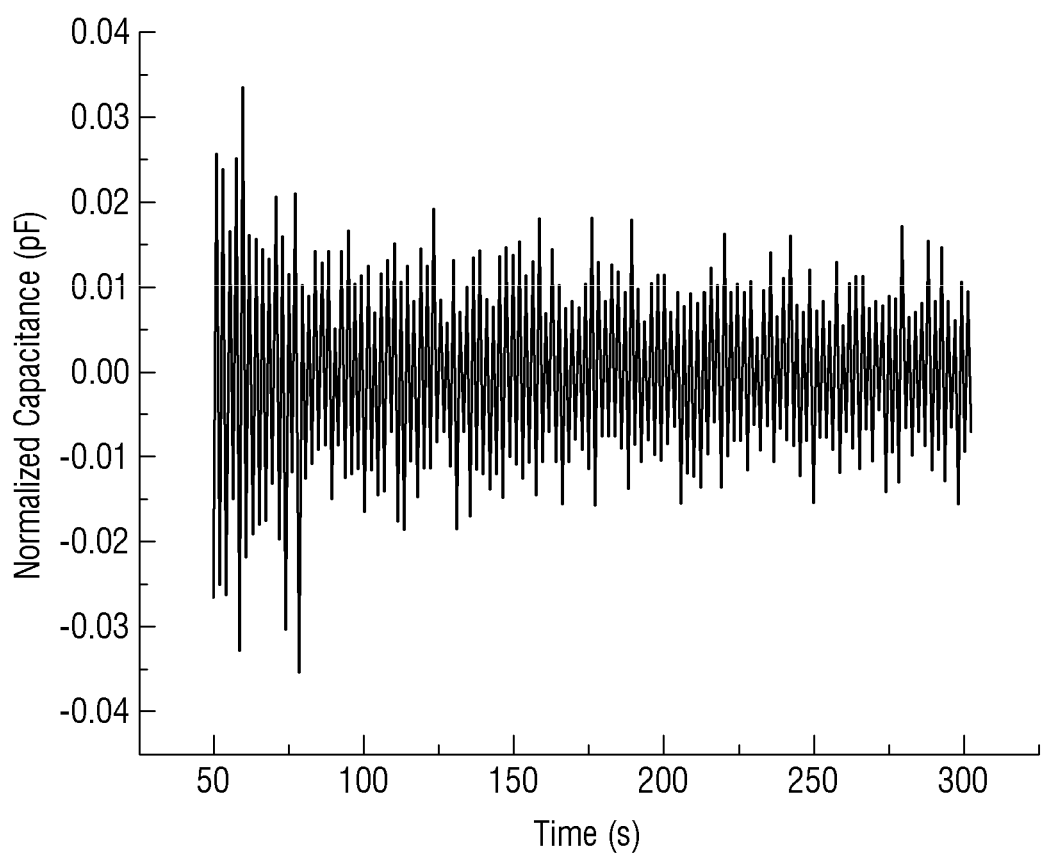
FIG. 17 is a graph illustrating a filtered heart rate area in the graph of FIG. 16 according to an embodiment.
Figure 18:
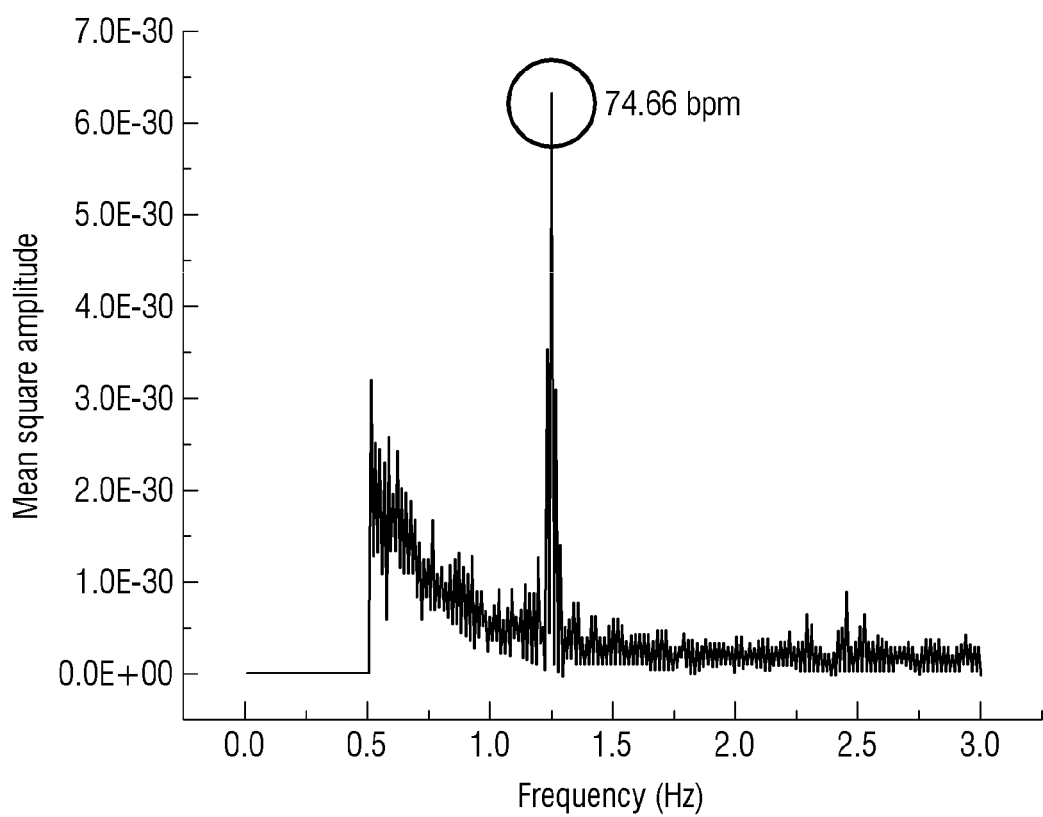
FIG. 18 is a graph illustrating the peak of a heart beat detected through Fourier transform in the graph of FIG. 17 according to an embodiment.
Figure 19:
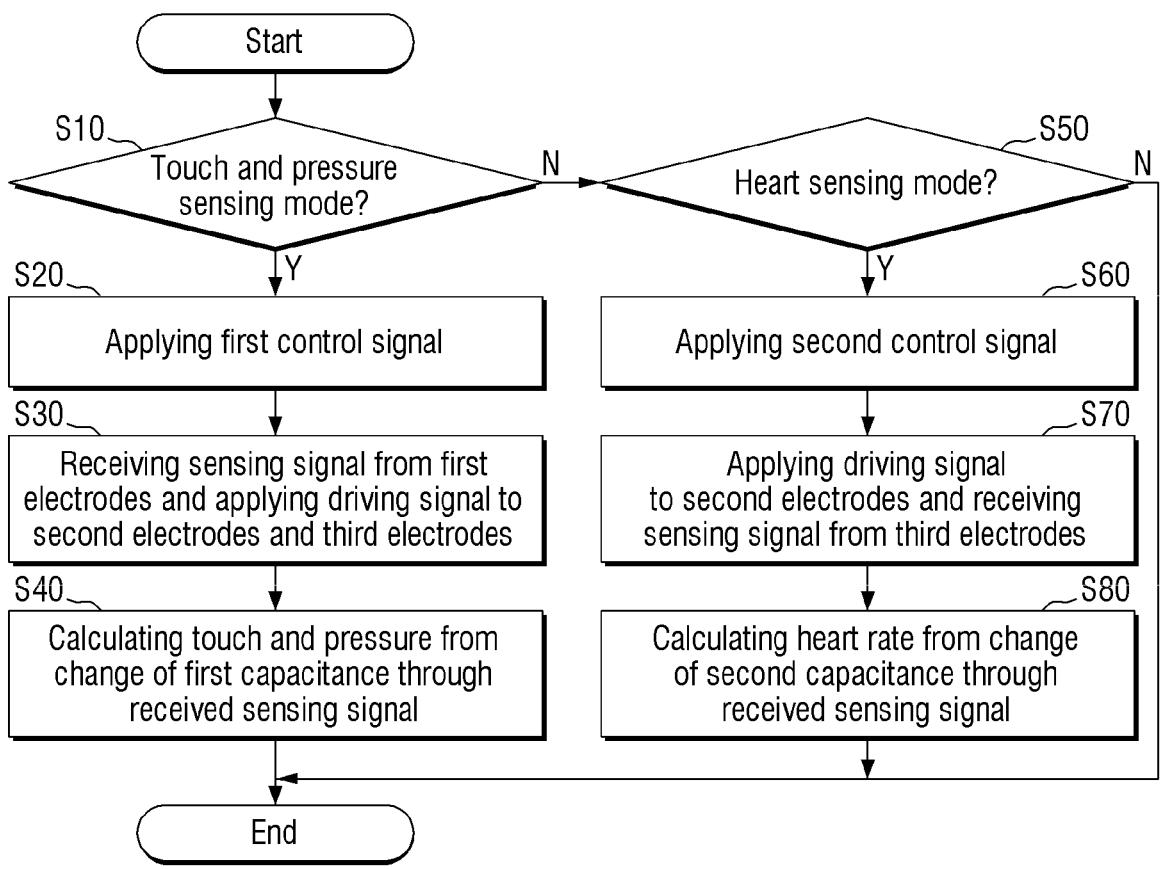
FIG. 19 is a block diagram schematically illustrating a method of sensing a touch input, a touch pressure, and a heart rate according to an embodiment.

FIG. 10 is a view schematically illustrating a touch input state according to an embodiment. FIG. 11 is a graph illustrating the change in a first capacitance when a touch is input according to an embodiment. FIG. 12 is a view schematically illustrating a touch input state according to an embodiment. FIG. 13 is a graph illustrating the change in a first capacitance when a touch is input according to an embodiment. FIG. 14 is a view schematically illustrating the formation of a second capacitance according to an embodiment. FIG. 15 is a view schematically illustrating the state of sensing a heart rate according to an embodiment. FIG. 16 is a graph illustrating the change in a second capacitance when a heart rate is detected according to an embodiment. FIG. 17 is a graph illustrating a filtered heart rate area in the graph of FIG. 16. FIG. 18 is a graph illustrating the peak of a heart beat detected through Fourier transform in the graph of FIG. 17. FIG. 19 is a block diagram schematically illustrating a method of sensing a touch input, a touch pressure, and a heart rate according to an embodiment.

Referring to FIGS. 6, 10, and 19, the controller 450 may determine whether the sensing unit SU is in a touch and pressure sensing mode (S10). For example, the controller 450 may transmit the first control signal CS1 to the first switches SW1 in the touch and pressure sensing mode (S20).

When the first switches SW1 are turned on, the third lines L3 may be connected to the third-first lines L3-1, sensing signals may be received from the first electrodes E1 connected to the first lines L1, driving signals may be applied to the second electrodes E2 connected to the second line L2, and driving signals may be applied to the third electrodes E3 connected to the third-first line L3-1 (S30). Accordingly, the sensing unit SU may sense a touch input and a touch pressure from the received sensing signals (S40).

Referring to FIGS. 10 and 11, in the touch input and pressure mode, a first capacitance C1 is formed between the first electrode E1 and the second electrode E2 and between the first electrode E1 and the third electrode E3 in the vertical direction (or Z-axis direction) perpendicular to the bottom face of the base BA, and the first capacitance C1 at the point at which the touch input is provided or the first capacitance C1 in the peripheral portion of the point is reduced when a user's finger F contacts the sensing unit SU, that is, when a touch input is generated. The first electrode E1 receives such an amount of change of the first capacitance C1, and the presence-position or absence of the touch input may be detected using the amount of change of the first capacitance C1.

Referring to FIGS. 12 and 13, in the touch input and pressure mode, a first capacitance C1 is formed between the first electrode E1 and the second electrode E2 and between the first electrode E1 and the third electrode E3 in the vertical direction, and the thickness of the first insulating layer IL1 is reduced from a first thickness d1 to a second thickness when a touch pressure is input in the vertical/third direction (Z-axis direction) by a user's finger, so that the first capacitance C1 at the point at which the touch pressure is provided or the first capacitance C1 in the peripheral portion of the point is increased. The first electrode E1 receives such an amount of change of the first capacitance C1, and the touch pressure may be detected using the change in the first capacitance C1. Since the amount of change of the first capacitance C1 is changed according the intensity of pressure, first pressure (gentle pressure) and second pressure (high pressure) may be distinguished and detected. The display device 10 may advantageously have different functions according to the first pressure (gentle pressure) and the second pressure (high pressure).

Referring to FIGS. 6, 14, 15, and 19, the controller 450 may determine whether the sensing unit SU is in a heart rate sensing mode (S50). For example, in the heart rate sensing mode, the second control signal CS2 may be transmitted to the second switches SW2 (S60).

When the second switches SW2 are turned on, the third lines L3 may be connected to the third-second lines L3-2, driving signals may be applied to the second electrodes E2 connected to the second line L2, and sensing signals may be received from the third electrodes E3 connected to the third-second lines L3-2 (S70). In some embodiments, a ground voltage may be applied to the first electrodes E1 connected to the first line L1. In some embodiments, a specific voltage may be applied to the first electrode E1 connected to the first line L1. A second capacitance C2, which is a fringe capacitance formed by a fringe field, may be formed between the second electrodes E2 and the third electrodes E3. The amount of change of the second capacitance C2 may be detected through the received sensing signal of the sensing unit SU, and a heart rate may be measured based on the amount of change of the second capacitance C2.

Referring to FIGS. 15 and 16, in the heart sensing mode, the second capacitance C2 is formed between the second electrode E2 and the third electrode E3, and the second capacitance C2 at the point at which the touch input is provided or the second capacitance C2 in the peripheral portion of the point is increased when a user's finger F contacts the sensing unit SU. The reason is that the dielectric constant over the second electrode E2 and the third electrode E3 is increased by the finger F. The third electrode E3 may receive the amount of change of the second capacitance C2.

In the graph of FIG. 16, minute vibration of the second capacitance C2 occurs during the contact due to the blood volume change according to the diastole and systole of a blood vessel of the finger F, and the second capacitance C2 may be used to measure the minute vibration.

Referring to the graph of FIG. 17, the minute vibration of the second capacitance C2 is filtered using a band pass filter having a range of 0.5 Hz to 3 Hz (30 bpm to 180 bpm), which is a heart rate range. Thus, filtered signals having a peak-to-peak of 0.02 pF to 0.06 pF may be extracted using the band pass filter.

Referring to FIG. 18, in the filtered signals of FIG. 17, a peak appears at a specific frequency through Fourier Transform, and a heart rate (74.66 bpm illustrated in FIG. 18) may be detected through the corresponding peak. Through this process, the sensing unit SU may measure the heart rate. The filtering and Fourier transform using the band pass filter may be performed by the second sensing driver 430, and the second sensing driver 430 may include a detector for filtering and Fourier transform.

Figure 20:
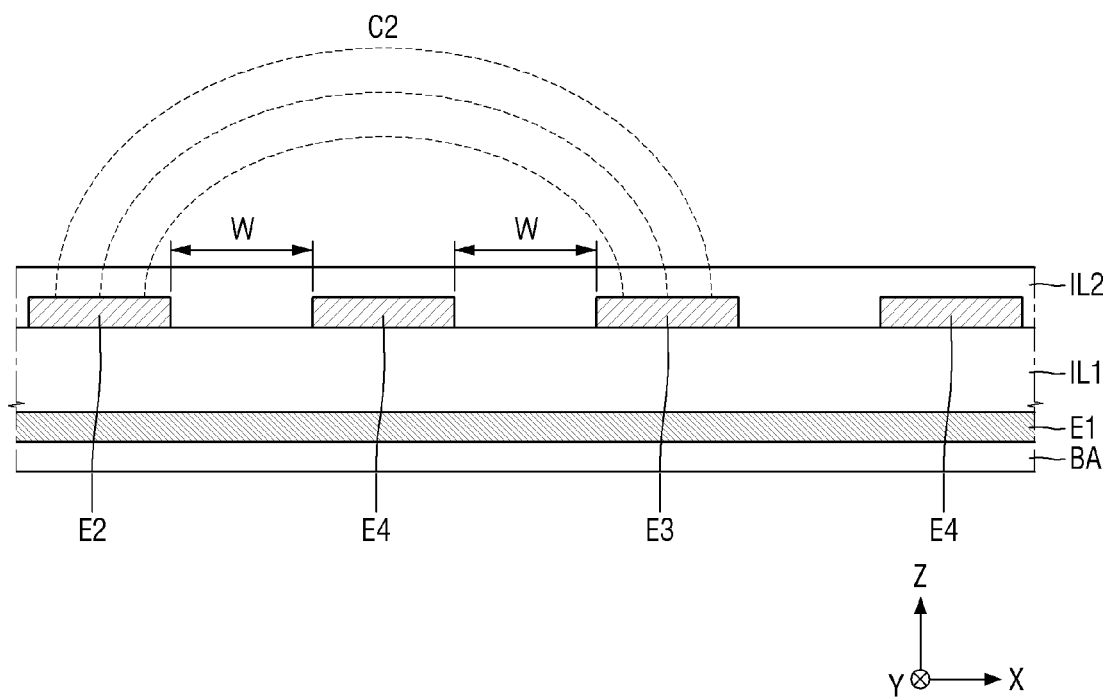
FIG. 20 is a view schematically illustrating an electrode structure according to an embodiment.
Figure 21:
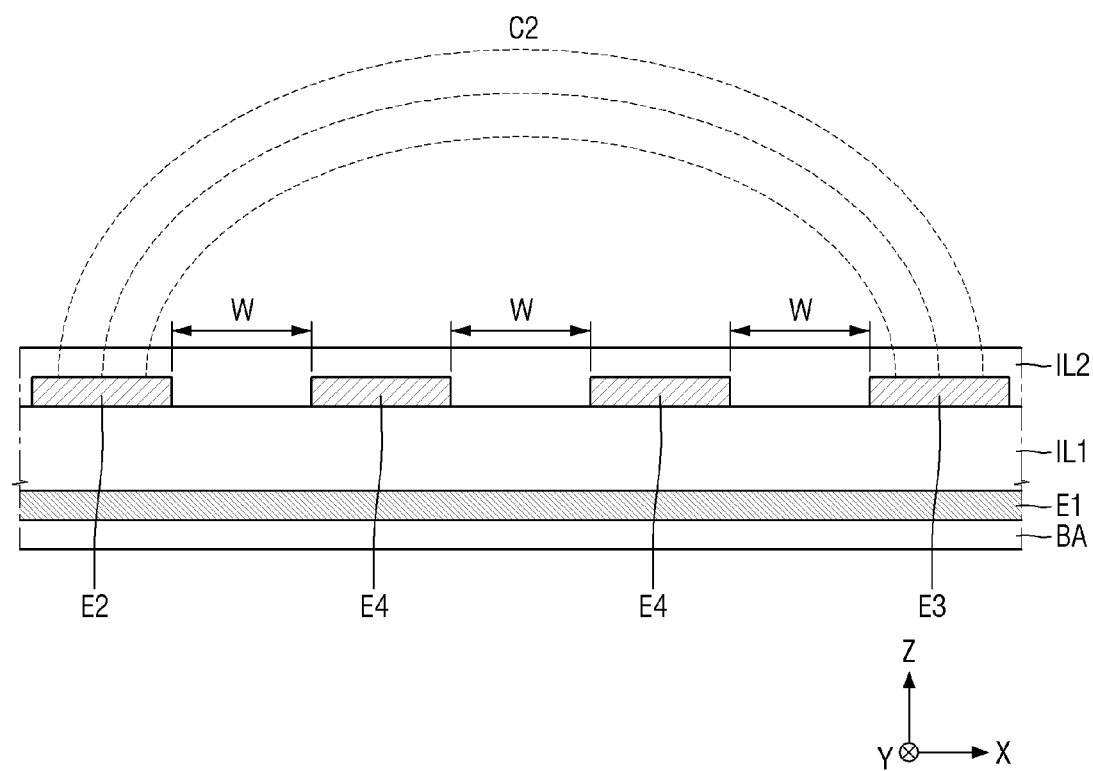
FIG. 21 is a view schematically illustrating an electrode structure according to an embodiment.

FIG. 20 is a view schematically illustrating an electrode structure according to an embodiment. FIG. 21 is a view schematically illustrating an electrode structure according to another embodiment. The embodiment of FIGS. 20 and 21 is different from the embodiment of FIG. 9 in that a fourth electrode E4 is further included.

Referring to FIG. 20, a second electrode E2, a fourth electrode E4, and a third electrode E3 may be disposed on the first insulating layer IL1. The second electrode E2, the fourth electrode E4, and the third electrode E3 may be sequentially disposed along the first direction (X-axis direction), and may be spaced apart from each other.

The distance W between the second electrode E2 and the fourth electrode E4 may be equal to the distance W between the fourth electrode E4 and the third electrode E3. The distance W may be in a range of 2 mm to 4 mm.

In the heart rate sensing mode, a second capacitance C2 may be formed between the second electrode E2 and the third electrode E3 in the substantially horizontal direction. A driving signal may be applied to the second electrode E2, and a sensing signal may be applied to the third electrode E3. A ground voltage may be applied to the first electrode E1 and the fourth electrode E4. The fourth electrode E4 may be disposed between the second electrode E2 and the third electrode E3 for increasing the measurement range of the heart rate. Although not shown, in the touch input and pressure sensing mode, a driving signal may be provided to each of the second electrode E2, the fourth electrode E4, and the third electrode E3, and the first electrode E1 may receive a sensing signal.

Referring to FIG. 21, a second electrode E2 and a third electrode E3 may be disposed on the first insulating layer IL1, and two fourth electrodes E4 may be disposed between the second electrode E2 and the third electrode E3. The second electrode E2, the first fourth electrode E4, the second fourth electrode E4, and the third electrode E3 may be spaced apart from each other.

The distance W between the second electrode E2 and the first fourth electrode E4, the distance W between the two fourth electrodes E4, and the distance W between the second fourth electrode E4 and the third electrode E3 may be equal to each other. The distance W may be in a range of 2 mm to 4 mm.

In the heart rate sensing mode, a second capacitance C2 may be formed between the second electrode E2 and the third electrode E3 in the substantially horizontal direction. A driving signal may be applied to the second electrode E2, and a sensing signal may be applied to the third electrode E3. A ground voltage may be applied to the first electrode E1 and the fourth electrodes E4. The two fourth electrodes E4 may be disposed between the second electrode E2 and the third electrode E3 for increasing the measurement range of the heart rate. Although not shown, in the touch input and pressure sensing mode, a driving signal may be provided to each of the second electrode E2, the fourth electrodes E4, and the third electrode E3, and the first electrode E1 may receive a sensing signal.

Figure 22:
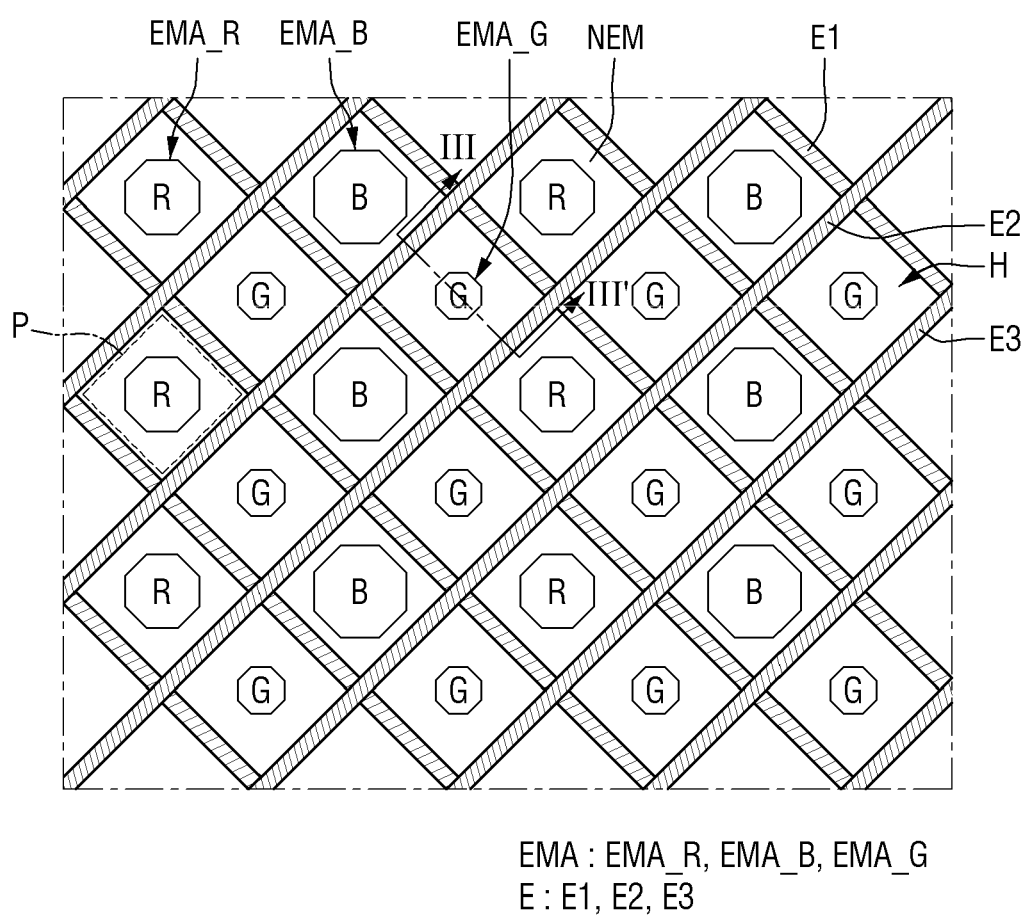
FIG. 22 is a view schematically showing structural relations between pixels of the display unit and electrodes of the sensing unit according to an embodiment.
Figure 23:
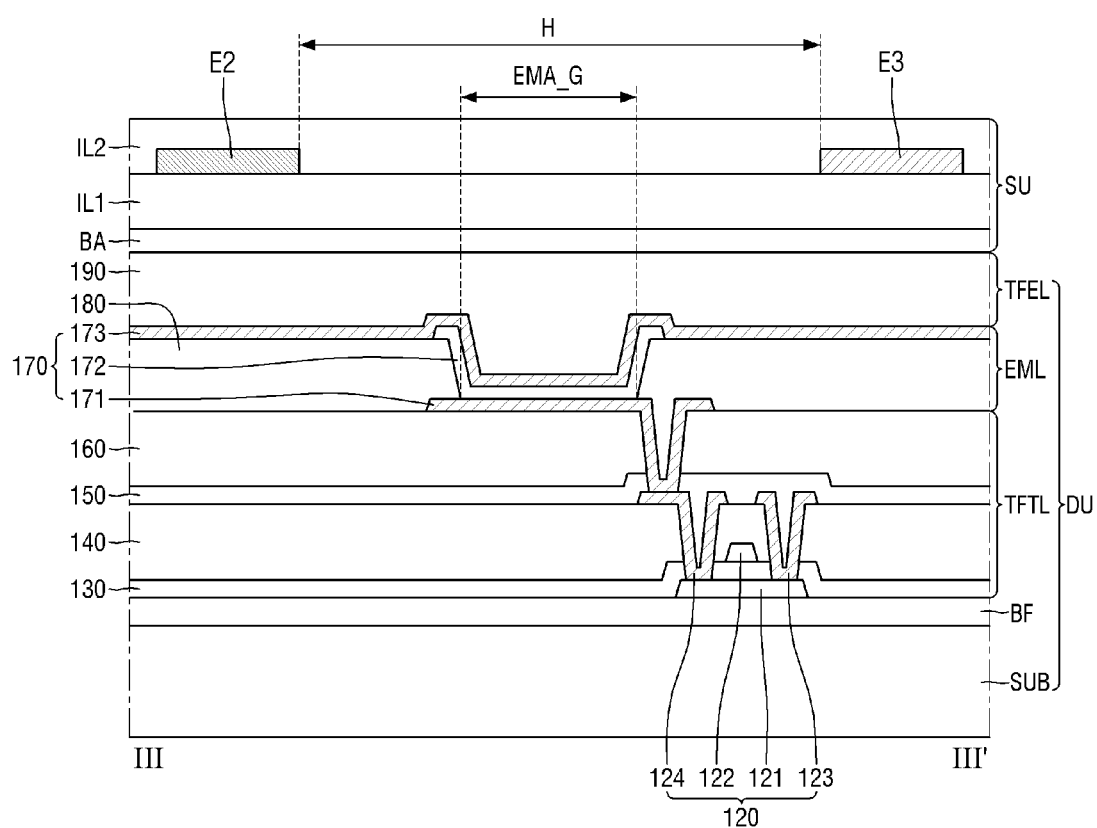
FIG. 23 is a cross-sectional view taken along the line III-III' of FIG. 22 according to an embodiment.

FIG. 22 is a view schematically showing structural relations between pixels of the display unit and electrodes of the sensing unit according to an embodiment. FIG. 23 is a cross-sectional view taken along the line III-III' of FIG. 22 according to an embodiment.

Referring to FIG. 22, the display unit (analogous to the display unit DU illustrated in FIG. 4) may include a plurality of pixels P. Each of the pixels P may include a light emitting area EMA and a non-light emitting area NEM.

The pixels P may include a first color pixel, a second color pixel, and a third color pixel. The color pixels P may be arranged in various ways according to embodiments. In an embodiment, the first color pixels (for example, red pixels) and the second color pixels (for example, blue pixels) are alternately arranged in first-type rows, and the third color pixels (for example, green pixels) may be arranged in second-type rows adjacent to (and between) the first-type rows. The pixels belonging to a second-type row may be staggered in a first direction with respect to the pixels belonging to a first-type row. The number of the third color pixels belonging to the second row may be twice the number of the first color pixels or the second color pixels belonging to the first row. The arrangement of a first-type row and a second-type row may be repeated along ta second direction.

The sizes of the light emitting areas EMA in the respective color pixels P may be different from each other. For example, the light emitting area EMA_B of a second color pixel may be larger than the light emitting area EMA_R of a first color pixel, and the light emitting area EMA_G of a third color pixel may be smaller than the light emitting area EMA_R of the first color pixel.

The shape of the light emitting area EMA of each color pixel P may be substantially octagonal. The shape of the light emitting area EMA of each color pixel P may be a circle, a rhombus, a polygon, or a polygon having round corners.

The second electrodes E2 and the third electrodes E3 may be parallel to each other, and the second electrodes E2 and the third electrodes E3 may intersect the first electrodes E1 to form holes H in a plan view of the display device.

A hole H may contain a light emitting area EMA in the plan view of the display device, and the area of the hole H may be larger than the area of the light emitting area EMA. The electrodes E may overlap the non-light emitting area NEM in the thickness direction of the display device, and the width of an electrode E may be smaller than the width of a non-light emitting area NEM. Through such a structure, light output from the light emitting area EMA of the display unit DU may be effectively transmitted through the sensing unit SU.

Referring to FIG. 23, the display device may include a display unit DU and a sensing unit SU disposed on the display unit DU.

The display unit DU may include a substrate SUB, a thin film transistor layer TFTL, a light emitting element layer EML, and a thin film encapsulation layer TFEL, which are sequentially disposed on the substrate SUB.

The substrate SUB is described with reference to FIG. 3.

The thin film transistor layer TFTL is formed on the substrate SUB. The thin film transistor layer TFTL includes thin film transistors 120, a gate insulating film 130, an interlayer insulating film 140, a protective film 150, and a planarization film 160.

A buffer layer BF may be formed on one surface of the substrate SUB. The buffer layer BF is formed on one surface of the substrate SUB so as to protect driving thin film transistors 120 and the organic light emitting layer 172 of the light emitting element layer EML from moisture permeating through the substrate SUB vulnerable to moisture permeation. The buffer layer BF may include a plurality of laminated inorganic films. For example, the buffer layer BF may be formed of a multi-layer film in which one or more inorganic layers, including a silicon nitride layer, a silicon oxynitride layer, a silicon oxide layer, a titanium oxide layer, and an aluminum oxide layer, are laminated. The buffer layer BF may be optional.

The thin film transistor 120 is formed on the buffer layer BF. The thin film transistor 120 includes an active layer 121, a gate electrode 122, a source electrode 123, and a drain electrode 124. FIG. 23 illustrates that the thin film transistor 120 may have a top gate structure in which the gate electrode 122 is located on the active layer 121. The thin film transistors 120 may have a bottom gate structure in which the gate electrode 122 is located beneath the active layer 121, or may have a double gate structure in which gate electrodes are located on and beneath the active layer 121.

The active layer 121 is formed on the buffer layer BF. The active layer 211 may include polycrystalline silicon, monocrystalline silicon, low-temperature polycrystalline silicon, amorphous silicon, or an oxide semiconductor. Examples of the oxide semiconductor may include a two-component compound (ABx), a three-component compound (ABxCy), and a four component compound (ABxCyDz), each containing indium (In), zinc (Zn), gallium (Ga), tin (Sn), titanium (Ti), aluminum (Al), hafnium (Hf), zirconium (Zr), or magnesium (Mg). For example, the active layer 121 may include ITZO (an oxide including indium, tin, and titanium) or IGZO (an oxide including indium, gallium, and tin). A light blocking layer for blocking external light incident on the active layer 121 may be formed between the buffer layer BF and the active layer 121.

The gate insulating film 130 may be formed on the active layer 211. The gate insulating film 130 may be formed of an inorganic layer, for example, a silicon nitride layer, a silicon oxynitride layer, a silicon oxide layer, a titanium oxide layer, or an aluminum oxide layer.

The gate electrode 122 and a gate line may be formed on the gate insulating film 130. The gate electrode 122 and the gate line may have a single-layer or multi-layer structure including at least one of molybdenum (Mo), aluminum (Al), chromium (Cr), gold (Au), titanium (Ti), nickel (Ni), neodymium (Nd) and copper (Cu), or an alloy of some of the metals.

The interlayer insulating film 140 may be formed on the gate electrode 122 and the gate line. The interlayer insulating film 140 may be/include an inorganic layer, for example, a silicon nitride layer, a silicon oxynitride layer, a silicon oxide layer, a titanium oxide layer, or an aluminum oxide layer.

The source electrode 123 and the drain electrode 124 may be formed on the interlayer insulating film 140. Each of the source electrode 123 and the drain electrode 124 may be connected to the active layer 211 through a contact hole that penetrates the gate insulating film 130 and the interlayer insulating film 140. The source electrode 123 and the drain electrode 124 may have a single-layer or multi-layer structure including at least one of molybdenum (Mo), aluminum (Al), chromium (Cr), gold (Au), titanium (Ti), nickel (Ni), neodymium (Nd) and copper (Cu), or an alloy of some of the metals.

The protective film 150 for insulating the thin film transistor 120 may be formed on the source electrode 123 and the drain electrode 124. The protective film 150 may be/include an inorganic layer, for example, a silicon nitride layer, a silicon oxynitride layer, a silicon oxide layer, a titanium oxide layer, or an aluminum oxide layer.

The planarization film 160 for planarizing a step due to the thin film transistor 120 may be formed on the protective film 150. The planarization film 160 may be/include an organic film including an acryl resin, an epoxy resin, a phenolic resin, a polyamide resin, or a polyimide resin.

A light emitting element layer EML is formed on the thin film transistor layer TFTL. The light emitting element layer EML includes light emitting elements 170 and a pixel defining film 180.

The light emitting elements 170 and the pixel defining film 180 are formed on the planarization film 160. Each of the light emitting elements 170 may include an anode electrode 171, a light emitting layer 172, and a cathode electrode 173.

The anode electrode 171 may be formed on the planarization film 160. The anode electrode 171 is connected to the source electrode 123 of the thin film transistor 120 through a contact hole penetrating the protective film 150 and the planarization film 160.

In a top emission structure in which light is emitted toward the cathode electrode 173 with respect to the organic light emitting layer 172, the anode electrode 171 may be formed of a metal material having high reflectance such as a laminate structure (Ti—Al—Ti) of aluminum and titanium, a laminate structure (ITO-Al-ITO) of aluminum and ITO, an APC alloy, or a laminate structure (ITO-APC-ITO) of an APC and ITO. The APC alloy is an alloy of silver (Ag), palladium (Pd), and copper (Cu).

In a bottom emission structure in which light is emitted toward the anode electrode 171 with respect to the organic light emitting layer 172, the anode electrode 171 may be formed of a transparent conductive material (TCO) such as ITO or IZO, which can transmit light, or a semi-transmissive conductive material such as magnesium (Mg), silver (Ag), or an alloy of magnesium (Mg) and silver (Ag). When the anode electrode 171 is formed of a semi-transmissive conductive material, light emission efficiency may be increased by microcavities.

The pixel defining film 180 may be formed on the planarization film 160 to divide the anode electrode 171 so as to define pixels. The pixel defining film 180 may cover the edge of the anode electrode 171. The pixel defining film 180 may be/include an organic film including an acryl resin, an epoxy resin, a phenolic resin, a polyamide resin, or a polyimide resin.

The second light emitting area EMA2 indicates an area where the anode electrode 171, the organic light emitting layer 172, and the cathode electrode 173 are sequentially laminated, and holes from the anode electrode 171 are combined with electrons from the cathode electrode 173 to emit light. Each of the light emitting areas EMA_R, EMA_G, and EMA_B may include a light emitting element 170.

The organic light emitting layer 172 is formed on the anode electrode 171 and the pixel defining film 180. The organic light emitting layer 172 may include an organic material to emit light of a predetermined color. For example, the organic light emitting layer 172 may include a hole transporting layer, an organic material layer, and an electron transporting layer.

The cathode electrode 173 is formed on the organic light emitting layer 172. The cathode electrode 173 may cover the organic light emitting layer 172. The cathode electrode 173 may be a common layer commonly formed in the light emitting areas EMA_R, EMA_G, and EMA_B. A capping layer may be formed on the cathode electrode 173.

In the top emission structure, the cathode electrode 173 may be formed of a transparent conductive material (TCO) such as ITO or IZO, which can transmit light, or a semi-transmissive conductive material such as magnesium (Mg), silver (Ag), or an alloy of magnesium (Mg) and silver (Ag). When the cathode electrode 173 is formed of a semi-transmissive conductive material, light emission efficiency may be increased by microcavities.

In the bottom emission structure, the cathode electrode 173 may be formed of a metal material having high reflectance such as a laminate structure (Ti—Al—Ti) of aluminum and titanium, a laminate structure (ITO-Al-ITO) of aluminum and ITO, an APC alloy, or a laminate structure (ITO-APC-ITO) of an APC and ITO. The APC alloy is an alloy of silver (Ag), palladium (Pd), and copper (Cu).

The thin film encapsulation layer TFEL is formed on the light emitting element layer EML. The thin film encapsulation layer TFEL includes an encapsulation film 190.

The encapsulation film 190 is disposed on the cathode electrode 173. The encapsulation film 190 may include at least one inorganic film to prevent oxygen or moisture from permeating the organic light emitting layer 172 and the cathode electrode 173. The encapsulation film 190 may include at least one organic film to protect the light emitting element layer EML from foreign matter such as dust. For example, the encapsulation film 190 may include a first inorganic film disposed on the cathode electrode 173, an organic film disposed on the first inorganic film, and a second inorganic film disposed on the organic film. The first inorganic film and the second inorganic film may be/include a silicon nitride layer, a silicon oxynitride layer, a silicon oxide layer, a titanium oxide layer, or an aluminum oxide layer. The organic film may be formed of an acryl resin, an epoxy resin, a phenolic resin, a polyamide resin, or a polyimide resin.

The sensing unit SU is disposed on the thin film encapsulation layer TFEL. For example, the base BA of the sensing unit SU may be disposed on the thin film encapsulation layer TFEL, such that the thin film encapsulation layer TFEL may be positioned between the base BA and the thin film transistor layer TFTL.

Many variations and modifications can be made to the described embodiments without substantially departing from the scope defined in the claims. The described embodiments are illustrative and not for purposes of limitation.

What is claimed is:

1. A sensing unit, comprising:
a base;
first electrodes arranged on the base, extending lengthwise individually in a first direction, and spaced apart from each other in a second direction different from the first direction;
a first insulating layer disposed on the first electrodes;
second electrodes electrically insulated from the first electrodes by the first insulating layer, extending lengthwise individually in the second direction, and spaced apart from each other in the first direction;
third electrodes electrically insulated from the first electrodes by the first insulating layer, extending lengthwise individually in the second direction, and electrically insulated from the second electrodes; and
a second insulating layer disposed on the second electrodes and the third electrodes,
wherein each of the first insulating layer and the second insulating layer includes polydimethylsiloxane (PDMS),
wherein the second electrodes and the third electrodes are alternately arranged in the first direction, and
wherein the third electrodes are configured to receive a driving signal in a first sensing mode and to transmit a sensing signal in a second sensing mode.

2. The sensing unit of claim 1, further comprising:
a sensing driving circuit providing signals to the first electrodes, the second electrodes, and the third electrodes;
first lines electrically connecting the first electrodes and the sensing driving circuit;
second lines electrically connecting the second electrodes and the sensing driving circuit; and
third lines electrically connecting the third electrodes and the sensing driving circuit,
wherein the third lines are electrically connected to the sensing driving circuit through first switches in the first sensing mode and are electrically connected to the sensing driving circuit through second switches in the second sensing mode.

3. The sensing unit of claim 2, further comprising:
a controller supplying control signals to the first switches and the second switches.

4. The sensing unit of claim 3,
wherein the first sensing mode is a touch input and pressure sensing mode,
wherein the second sensing mode is a heart sensing mode,
wherein the controller supplies a first control signal to the first switches to turn on the first switches in a touch input and pressure sensing mode,
wherein the controller supplies a second control signal to the second switches to turn on the second switches in a heart rate sensing mode, and
wherein the sensing driving circuit provides the driving signal to the third lines when the first switches are turned on and receives the sensing signal from the third lines when the second switches are turned on.

5. The sensing unit of claim 4,
wherein the sensing driving circuit receives the sensing signal from the first lines and provides the driving signal to the second lines in the touch input and pressure sensing mode, and
wherein the sensing driving circuit provides a ground voltage to the first lines and provides the driving signal to the second lines in the heart rate sensing mode.

6. The sensing unit of claim 1,
wherein the second electrodes and the third electrodes are spaced apart from each other in the first direction, and
wherein a distance between a second electrode and an immediately neighboring third electrode is in a range of about 2 mm to about 4 mm.

7. The sensing unit of claim 1,
wherein the first electrodes, the second electrodes, and the third electrodes include at least one of a silver nanowire, a metal mesh, and a carbon nanotube (CNT).

8. The sensing unit of claim 1, further comprising:
first auxiliary electrodes arranged on one side of the second electrodes; and
second auxiliary electrodes arranged on one side of the third electrodes,
wherein the first auxiliary electrodes and the second auxiliary electrodes are alternately arranged and are spaced apart from each other, and
wherein a distance between a first auxiliary electrode and an immediately neighboring second auxiliary electrode is in a range of about 10 um to about 500 um.

9. A display device, comprising:
a display unit;
a sensing unit disposed on the display unit; and
a window member disposed on the sensing unit,
wherein the sensing unit comprises:
a base;

first electrodes arranged on the base, extending lengthwise individually in a first direction, and spaced apart from each other in a second direction different from the first direction;

a first insulating layer disposed on the first electrodes;

second electrodes electrically insulated from the first electrodes by the first insulating layer, extending lengthwise individually in the second direction, and spaced apart from each other in the first direction;

third electrodes electrically insulated from the first electrodes by the first insulating layer, extending lengthwise individually in the second direction, and electrically insulated from the second electrodes; and a second insulating layer disposed on the second electrodes and the third electrodes, wherein each of the first insulating layer and the second insulating layer includes polydimethylsiloxane (PDMS), wherein the second electrodes and the third electrodes are alternately arranged in the first direction, and wherein the third electrodes are configured to receive a driving signal in a first sensing mode and to transmit a sensing signal in a second sensing mode.

10. The display device of claim 9, further comprising:

a sensing driving circuit providing signals to the first electrodes, the second electrodes, and the third electrodes;

first lines electrically connecting the first electrodes and the sensing driving circuit;

second lines electrically connecting the second electrodes and the sensing driving circuit; and third lines electrically connecting the third electrodes and the sensing driving circuit, wherein the third lines are electrically connected to the sensing driving circuit through first switches in the first sensing mode and are electrically connected to the sensing driving circuit through second switches in the second sensing mode.

11. The display device of claim 10, further comprising:

a controller supplying control signals to the first switches and the second switches.

12. The display device of claim 11, wherein the first sensing mode is a touch input and pressure sensing mode, wherein the second sensing mode is a heart sensing mode, wherein the controller supplies a first control signal to the first switches to turn on the first switches in a touch input and pressure sensing mode, wherein the controller supplies a second control signals to the second switches to turn on the second switches in a heart rate sensing mode, and wherein the sensing driving circuit provides the driving signal to the third lines when the first switches are turned on and receives the sensing signal from the third lines when the second switches are turned on.

13. The display device of claim 12, wherein the sensing driving circuit receives the sensing signal from the first lines and provides the driving signal to the second lines in the touch input and pressure sensing mode, and wherein the sensing driving circuit provides a ground voltage to the first lines and provides the driving signal to the second lines in the heart rate sensing mode.

14. The display device of claim 9, wherein the second electrodes and the third electrodes are spaced apart from each other in the first direction, and wherein a distance between a second electrode and an immediately neighboring third electrode is in a range of about 2 mm to about 4 mm.

15. The display device of claim 14, wherein the display unit comprises:

a substrate;

a thin film transistor layer disposed on the substrate;

a light emitting element layer disposed on the thin film transistor layer; and a thin film encapsulation layer disposed between the light emitting element layer and the base of the sensing unit.

16. A method of sensing performed by a display device, the method comprising:

sensing a change of a first capacitance in a vertical direction perpendicular to a face of the display device by providing a driving signal to at least one switch-connected electrode for sensing of a touch on the display device; and sensing a change of a second capacitance, which is a fringe capacitance, by receiving a sensing signal from the at least one switch-connected electrode for sensing of a heart rate.

17. The method of claim 16, wherein the display device comprises: a base; first electrodes arranged on the base, extending lengthwise individually in a first direction different from the vertical direction, and spaced apart from each other in a second direction different from the first direction and the vertical direction; a first insulating layer disposed on the first electrodes; second electrodes electrically insulated from the first electrodes by the first insulating layer, extending lengthwise individually in the second direction, and spaced apart from each other in the first direction; and third electrodes including the at least one switch-connected electrode, electrically insulated from the first electrodes by the first insulating layer, extending lengthwise individually in the second direction, and electrically insulated from the second electrodes, wherein the second electrodes and the third electrodes are alternately arranged in the first direction, and wherein the sensing of the touch further comprises:

receiving the sensing signal from the first electrodes; and providing the driving signal to the second electrodes and the third electrodes.

18. The method of claim 17, wherein the sensing of the heart rate further includes: providing the driving signal to the second electrodes; and receiving the sensing signal from the third electrodes.

19. The method of claim 18, wherein the sensing of the heart rate further includes providing a ground voltage to the first electrodes.

* * * * *